United States Patent
Ishii et al.

(10) Patent No.: US 6,429,314 B1
(45) Date of Patent: Aug. 6, 2002

(54) METHODS OF ACYLATING ADAMANTANE, TRICYCLO[5.2.1.0$^{2,6}$], AND DECALIN COMPOUNDS

(75) Inventors: Yasutaka Ishii, Takatsuki; Tatsuya Nakano; Naruhisa Hirai, both of Himeji, all of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/402,898

(22) PCT Filed: Feb. 10, 1999

(86) PCT No.: PCT/JP99/00567

§ 371 (c)(1),
(2), (4) Date: Oct. 13, 1999

(87) PCT Pub. No.: WO99/41219

PCT Pub. Date: Aug. 19, 1999

(30) Foreign Application Priority Data

Feb. 13, 1998 (JP) .............................. 10-48880
Mar. 27, 1998 (JP) .......................... 10-100458
Dec. 11, 1998 (JP) .......................... 10-353620

(51) Int. Cl.$^7$ ........................ C07D 221/02; C07C 35/22
(52) U.S. Cl. ...................... 546/112; 568/818
(58) Field of Search ....................... 546/112

(56) References Cited

U.S. PATENT DOCUMENTS

| 5,480,887 A | 1/1996 | Hornback et al. .......... 514/301 |
| 5,504,104 A | 4/1996 | Ellsworth et al. ........... 534/455 |
| 5,510,375 A | 4/1996 | Domagala et al. .......... 514/457 |

FOREIGN PATENT DOCUMENTS

| JP | A61-238733 | 10/1986 |
| JP | A7-502970  | 3/1995  |
| JP | A9-327626  | 12/1997 |
| WO | WO 9740833 | 3/1991  |

OTHER PUBLICATIONS

Murray, Robert W.; Gu, Hong, J. Org. Chem 1995, vol. 60 No. 17, P. 5673–5677.
Matsuo, A.; Nozaki, H.; Nakayama, M.; Kushi, Y.; Hayashi, S.; Kamijo, K., Tetrahedron Lett. 1975, No. 4, p. 241–244.
Swallow, D.L.; Edwards, P.N.; Finter, N.B. Ann. N.Y. Acad. Sci. 1970, vol. 173 Art. 1, p. 292–299.
Bok et al, Tetrahedron, 1979, vol. 35, pp. 267–272, esp. p. 268.

*Primary Examiner*—Deborah C. Lambkin
(74) *Attorney, Agent, or Firm*—Birch, Stewart, Kolasch & Birch, LLP

(57) ABSTRACT

An acylating agent of the invention includes (A) a 1,2-dicarbonyl compound or its hydroxy reductant, (B) oxygen, and (C) at least one compound selected from (c1) a metallic compound and (C2) N-hydroxyphthalimide or another imide compound. As the 1,2-dicarbonyl compound or its hydroxy reductant (A), biacetyl, 2,3-butanediolor the like canbeused. As the metallic compound (c1), cobalt acetate, or another cobalt compound, for example, can be employed. By reacting an adamantane derivative or another compound having a methine carbon atom with the acylating agent, an acyl group can be introduced to the methine carbon atom with efficiency.

24 Claims, No Drawings

METHODS OF ACYLATING ADAMANTANE, TRICYCLO[5.2.1.0$^{2,6}$], AND DECALIN COMPOUNDS

This application is the national phase under 35 U.S.C. §371 of PCT International Application No. PCT/JP99/00567 which has an International filing date of Feb. 10, 1999, which designated the United States of America.

TECHNICAL FIELD

The present invention relates to acylating agents which are useful for the production of compounds each containing an acyl group such as acetyl group, to acylation methods using the acylating agents, to methods for the production of acyl group-containing compounds, to methods for the production of vinyl group-containing polycyclic compounds, and to methods for the production of epoxy group-containing polycyclic compounds. It also relates to adamantane derivatives, tricyclo[5.2.1.0$^{2,6}$]decane derivatives and decalin derivatives which are useful as, for example, monomers or their materials for functional polymers, and to methods for the production of these compounds.

BACKGROUND ART

As a method for the introduction of an acyl group directly to a carbon atom of an organic substrate is known a process using an acid halide. For example, a β-keto-ester is obtained by reacting a ketone and an acid halide in the presence of a base. According to this method, however, it is difficult to introduce an acyl group to a carbon atom not activated such as a carbon atom at the bridgehead position of a polycyclic compound, although a substrate which is activated by, for example, a carbonyl group can be acylated with facility.

J. Org. Chem. 1978, 43, 2370 and J. Org. Chem. 1988, 53, 4369 disclose methods comprising the step of reacting an adamantane derivative with biacetyl under light irradiation to obtain a 1-acetyladamantane derivative. This method, however, requires a special apparatus and, in addition, is low in yield.

As a method for the introduction of an acyl group to the bridgehead position of adamantane, there is known a process comprising the steps of reacting 1-carboxyladamantane with thionyl chloride to give a corresponding acid chloride, reacting this compound with ethyl malonate in the presence of a base to form 1-[2-bis (ethoxycarbonyl) acetyl] adamantane, and subsequently decomposing this compound with an acid to give 1-acetyladamantane. This process, however, requires a large number of steps, and is commercially disadvantageous.

As has been described, there has been no method for the introduction of an acyl group directly to a not-activated carbon atom with facility, up to this time.

On the other hand, adamantane derivatives, tricyclo [5.2.1.0$^{2,6}$ decane derivatives and decalin derivatives, in which acetyl group or another acyl group is introduced to its bridgehead position, are useful as manufacturing materials for, for example, vinyl group- or epoxy group-containing polycyclic compounds which serve as monomers for functional polymers. Demands have therefore been made to provide simple and efficient methods for the production of these compounds.

DISCLOSURE OF THE INVENTION

Accordingly, it is an object of the present invention to provide an acylating agent and a method for acylation which can introduce an acyl group directly even to a not-activated carbon atom with facility.

Another object of the invention is to provide an acylating agent and a method for acylation which can introduce an acyl group to a methine carbon atom with efficiency.

A further object of the invention is to provide a method for the industrial production of acyl group-containing compounds with efficiency.

It is another object of the invention to provide a simple and efficient method for the production of adamantane derivatives, tricyclo [5.2.1.0$^{2,6}$]decane derivatives, decalin derivatives, and other polycyclic compounds each of which has an acyl group, vinyl group or epoxy group.

Yet another object of the invention is to provide novel adamantane derivatives, tricyclo [5.2.1.0$^{2,6}$] decane derivatives and decalin derivatives.

After intensive investigations to achieve the above objects, the present inventors found that a combination use of a 1,2-dicarbonyl compound or its hydroxy reductant, oxygen and a metallic compound or the like can introduce an acyl group even to a not-activated carbon atom, such as a carbon atom at the bridgehead position of a polycyclic compound, with facility and efficiency. The present invention has been accomplished based on the above finding.

To be more specific, an acylating agent of the invention is composed of (A) a 1,2-dicarbonyl compound or its hydroxy reductant, (B) oxygen, and (C) at least one compound selected from (C1) a metallic compound and (C2) an imide compound represented by the following formula (1):

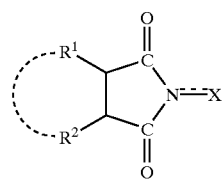

wherein each of R$^1$ and R$^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, or R$^1$ and R$^2$ may together form a double bond, or an aromatic or nonaromatic ring; X is an oxygen atom or a hydroxyl group; and to the aforementioned R$^1$, R$^2$, or to the double bond or aromatic or nonaromatic ring formed together by R$^1$ and R$^2$, one or two N-substituted cyclic imido groups indicated in the formula (1) may be bonded).

Furthermore, according to an acylation method of the invention, an organic substrate is reacted with the aforementioned acylating agent to form an acyl group-containing compound.

According to a method for the production of acyl group-containing compounds of the invention, an organic substrate is reacted with the aforementioned acylating agent to give an acyl group-containing compound.

Furthermore, according to a method for the production of adamantane derivatives of the invention, an adamantane derivative represented by the following formula (3):

(3)

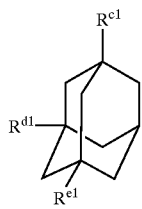

wherein each of $R^{c1}$, $R^{d1}$ and $R^{e1}$ is, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, or an acyl group; and of carbon atoms constituting the adamantane skeleton, the other carbon atoms than those at the bridgehead positions may each have a substituent) is reacted with the aforementioned acylating agent to give a compound represented by the following formula (4):

(4)

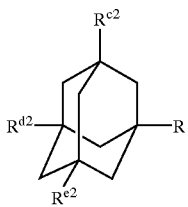

(wherein R is an acyl group, and each of $R^{c2}$, $R^{d2}$, and $R^{e2}$ is, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, or an acyl group; and of carbon atoms constituting the adamantane skeleton, the other carbon atoms than those at the bridgehead positions may have a substituent).

An adamantane derivative of the invention is represented by the following formula (7):

(7)

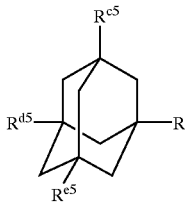

(wherein R is an acyl group, $R^{c5}$ is a hydroxyl group, or an acyl group, and each of $R^{d5}$ and $R^{e5}$ is, identical to or different from each other, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, or an acyl group; and of carbon atoms constituting the adamantane skeleton, the other carbon atoms than those at the bridgehead positions may each have a substituent).

In a method for the production of tricyclo $[5.2.1.0^{2,6}]$ decane derivatives according to the invention, a tricyclo $[5.2.1.0^{2,6}]$ decane derivative represented by the following formula (11):

(11)

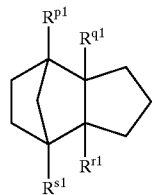

(wherein each of $R^{p1}$, $R^{q1}$, $R^{r1}$ and $R^{s1}$ is, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, or an acyl group, provided that at least one of $R^{p1}$, $R^{q1}$, $R^{r1}$ and $R^{s1}$ is a hydrogen atom; and of carbon atoms constituting the tricyclodecane skeleton, the other carbon atoms than those at the bridgehead positions may each have a substituent) is reacted with the aforementioned acylating agent to acylate a bridgehead position, and thereby to give a compound represented by the following formula (12):

(12)

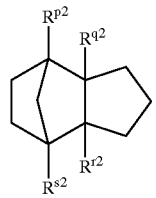

(wherein each of $R^{p2}$, $R^{q2}$, $R^{r2}$ and $R^{s2}$ is, identical to or different from one another, a hydrogen atom, a halogen atom, an alkyl group, a hydroxy group which may be protected by a protective group, a hydroxymethyl group which may be protected by a protective group, an amino group which may be protected by a protective group, a carboxyl group which may be protected by a protective group, a nitro group, or an acyl group, provided that at least one of $R^{p2}$, $R^{r2}$ and $R^{s2}$ is an acyl group; and of carbon atoms constituting the tricyclodecane skeleton, the other carbon atoms than those at the bridgehead positions may each have a substituent).

A tricyclo$[5.2.1.0^{2,6}]$decane derivative of the invention is a compound represented by the following formula (12):

(12)

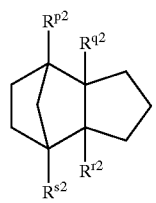

(wherein each of $R^{p2}$, $R^{q2}$, $R^{r2}$ and $R^{s2}$ is, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, or an acyl group, provided that at least one of $R^{p2}$, $R^{q2}$, $R^{r2}$ and $R^{s2}$ is an acyl group; and of carbon atoms constituting the tricyclodecane skeleton, the other carbon atoms than those at the bridgehead positions may each have a substituent).

In a method for the production of decalin derivatives according to the invention, a decalin derivative represented by the following formula (13):

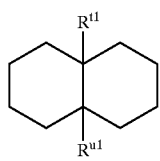

(13)

(wherein each of $R^{r1}$ and $R^{u1}$ is, identical to or different from each other, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, or an acyl group, provided that at least one of $R^{r1}$ and $R^{u1}$ is a hydrogen atom; and of carbon atoms constituting the decalin skeleton, the other carbon atoms than those at the bridgehead positions may each have a substituent). is reacted with the aforementioned acylating agent to acylate a bridgehead position, and thereby to give a compound represented by the following formula (14):

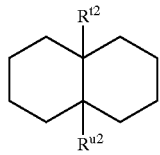

(14)

(wherein each of $R^{r2}$ and $R^{u2}$ is, identical to or different from each other, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, or an acyl group, provided that at least one of $R^{r2}$ and $R^{u2}$ is an acyl group; and of carbon atoms constituting the decalin skeleton, the other carbon atoms than those at the bridgehead positions may each have a substituent) A decalin derivative of the invention is represented by the following formula (14):

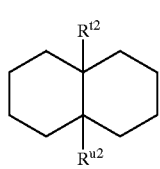

(14)

(wherein each of $R^{r2}$ and $R^{u2}$ is, identical to or different from each other, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, or an acyl group, provided that at least one of $R^{r2}$ and $R^{u2}$ is an acyl group; and of carbon atoms constituting the decalin skeleton, the other carbon atoms than those at the bridgehead positions may each have a substituent) According to a method for the production of vinyl group-containing polycyclic compounds of the invention, a polycyclic compound represented by the following formula (15):

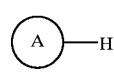

(15)

(wherein the ring A is a polycyclic group having a methine carbon atom at the bridgehead position, and the single bond indicated in the formula is bonded to the bridgehead position) is reacted with an acylating agent being composed of (A1) a 1,2-dicarbonyl compound or its hydroxy reductant represented by the following formula (2b)

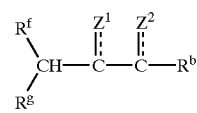

(2b)

(wherein each of $R^f$, $R^g$ and $R^b$ is, identical to or different from one another, a hydrogen atom, a hydrocarbon group or a heterocyclic group; and each of $Z^1$ and $Z^2$ is, identical to or different from each other, an oxygen atom or a hydroxyl group) (B) oxygen, and (C) at least one compound selected from (C1) a metallic compound and (C2) an imide compound represented by the following formula (1):

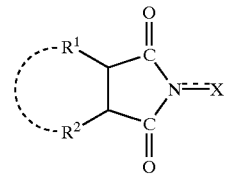

(1)

(wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may together form a double bond, or an aromatic or nonaromatic ring; X is an oxygen atom or a hydroxyl group; and to the aforementioned $R^1$, $R^2$, or to the double bond or aromatic or nonaromatic ring formed together by $R^1$ and $R^2$, one or two N-substituted cyclic Imido groups indicated in the formula (1) may be bonded) to form a compound represented by the following formula (16)

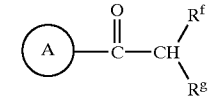

(16)

(wherein the ring A, $R^f$ and $R^g$ have the same meanings as defined above), the obtained compound represented by the formula (16) is reduced to give a compound represented by the following formula (17):

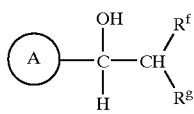
(17)

(wherein the ring A, $R^f$ and $R^g$ have the same meanings as defined above), and this compound is substituted to dehydration reaction to give a compound represented by the following formula (18):

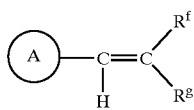
(18)

(wherein the ring A, $R^f$ and $R^g$ have the same meanings as defined above).

According to a method for the production of epoxy group-containing polycyclic compounds of the invention, the vinyl group-containing polycyclic compound obtained by the above method and represented by the formula (18) is reacted with an oxidizing agent to give a compound represented by the following formula (19):

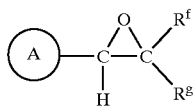
(19)

(wherein the ring A, $R^f$ and $R^g$ have the same meanings as defined above).

Another adamantane derivative of the invention is represented by the following formula (20):

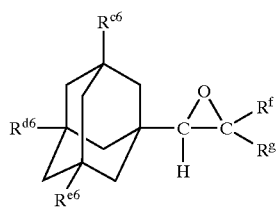
(20)

(wherein each of $R^{c6}$, $R^{d6}$, and $R^{e6}$ is, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, an acyl group, a hydroxymethyl group which may have a substituent, a vinyl group which may have a substituent, or an epoxy group which may have a substituent, provided that $R^{c6}$, $R^{d6}$, and $R^{e6}$ are not concurrently hydrogen atoms; each of $R^f$ and $R^g$ is, identical to or different from each other, a hydrogen atom, a hydrocarbon group or a heterocyclic group; and of carbon atoms constituting the adamantane skeleton, the other carbon atoms than those at the bridgehead positions may each have a substituent).

The term "protective group" as used in the present description is used in a wide concept, and includes a group derived from a free functional group, as well. The protective group may be incapable of leaving.

BEST MODE FOR CARRYING OUT THE INVENTION

[1,2-Dicarbonyl compound or its hydroxy reductant (A)]

The 1,2-dicarbonyl compound or its hydroxy reductant (hydroxy reducing form) (A) includes compounds represented by the following formula (2):

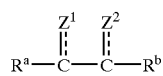
(2)

(wherein each of $R^a$ and $R^b$ is, identical to or different from each other, a hydrogen atom, a hydrocarbon group or a heterocyclic group, or $R^a$ and $R^1$ may together form a ring with adjacent two carbon atoms; and each of $Z^1$ and $Z^2$ is, identical to or different from each other, an oxygen atom or a hydroxyl group).

Hydrocarbon groups in $R^a$ and $R^1$ include methyl, ethyl, propyl, isopropyl, butyl, isobutyl, s-butyl, t-butyl, pentyl, hexyl, octyl, decyl, tetradecyl, hexadecyl, octadecyl, allyl groups and other straight- or branched-chain aliphatic hydrocarbon groups (alkyl groups, alkenyl groups and alkynyl groups) each having about 1 to 20 (preferably 1 to 10, and typically 1 to 6) carbon atoms; cyclopentyl, cyclohexyl groups and other alicyclic hydrocarbon groups (cycloalkyl groups and cycloalkenyl groups) each having about 3 to 8 carbon atoms; phenyl, naphthyl groups and other aromatic hydrocarbon groups (aryl groups) each having about 6 to 14 carbon atoms.

Heterocycles in the heterocyclic group include, for example, tetrahydrofuran, pyrrolidine, piperidine, piperazine, morpholine, indoline, furan, oxazole, thiophene, pyrrole, pyrazole, imidazole, pyridine, pyridazine, pyrimidine, pyrazine, indole, quinoline and other heterocycles (including condensed rings) each having about 3 to 15 members (preferably 5 to 12 members, and more preferably 5 or 6 members) and each containing 1 to 3 of at least one hetero atom selected from a nitrogen atom, an oxygen atom and a sulfur atom.

The hydrocarbon group and heterocyclic group may have a variety of substituents including, for instance, a halogen atom, an oxo group, a hydroxyl group, a substituted oxo group (e.g., an alkoxy group, an aryloxy group, an acyloxy group), a carboxyl group, a substituted oxycarbonyl group, a substituted or unsubstituted carbamoyl group, a cyano group, a nitro group, a substituted or unsubstituted amino group, an alkyl group, a cycloalkyl group, an aryl group (e.g., phenyl or naphthyl group), or a heterocyclic group. The groups $R^a$ and $R^b$ are often identical with each other.

As the ring formed together by $R^a$ and $R^b$ with the adjacent two carbon atoms, there may be mentioned cyclopentane ring, cyclohexane ring and other cycloalkane rings each having about 3 to 15 members (preferably 5 or 6 members). The ring may have, for instance, any of the aforementioned substituents.

Each of $Z^1$ and $Z^2$ represents an oxygen atom or a hydroxyl group, and the bond between the carbon atom and $Z^1$ or $Z^2$ is a single bond or a double bond.

Of compounds represented by the formula (2), preferred are compounds represented by the following formula (2a):

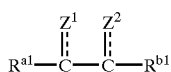
(2a)

(wherein each of $R^{a1}$ and $R^{b1}$ is, identical to or different from each other, an alkyl group having 1 to 4 carbon atoms, a cycloalkyl group or an aryl group, or $R^{a1}$ and $R^{b1}$ may together form a ring with adjacent two carbon atoms; and each of $Z^1$ and $Z^2$ is, identical to or different from each other, an oxygen atom or a hydroxyl group).

Typically preferred $R^{a1}$ and $R^{b1}$ are methyl group or ethyl group, in particular, methyl group. The groups $R^{a1}$ and $R^{b1}$ are often identical with each other.

As preferable concrete examples of the 1,2-dicarbonyl compound, there may be mentioned biacetyl (2,3-butanedione), 2,3-pentanedione, 3,4-hexanedione, bibenzoyl (benzyl), acetylbenzoyl, cyclopentane-1,2-dione, cyclohexane-1,2-dione and other α-diketones. Of these compounds, biacetyl or the like is preferable. Preferred illustrative hydroxy reductants of the 1,2-dicarbonyl compounds include acetoin, benzoin, and other α-keto-alcohols; 2,3-butanediol, 2,3-pentanediol, and other vicinal diols. Among them, acetoin and 2,3-butanediol are typically desirable.

Oxygen (B)

The oxygen (B) may be either molecular oxygen or active oxygen (oxygen radical). The molecular oxygen includes, but is not limited to, pure oxygen, and oxygen diluted with an inert gas such as nitrogen, helium, argon or carbon dioxide, as well as air. As the oxygen (B), molecular oxygen is frequently used.

Metallic Compound (C1)

Metallic elements to constitute the metallic compound (C1) are not especially limited, and can be any metallic element of Groups 1 to 15 of the Periodic Table of Elements. In the present description, the term "metallic element" also means and includes boron, B. Examples of the metallic elements include, of the Periodic Table of Elements, Group 1 elements (e.g., Li, Na, K), Group 2 elements (e.g., Mg, Ca, Sr, Ba), Groups 3 elements (e.g., Sc, lanthanoid elements, actinoid elements), Group 4 elements (e.g., Ti, Zr, Hf), Group 5 elements (e.g., V), Group 6 elements (e.g., Cr, Mo, W), Group 7 elements (e.g., Mn), Group 8 elements (e.g., Fe, Ru), Group 9 elements (e.g., Co, Rh), Group 10 elements (e.g., Ni, Pd, Pt), Group 11 elements (e.g., Cu), Group 12 elements (e.g., Zn), Groups 13 elements (e.g., B, Al, In), Group 14 elements (e.g., Sn, Pb), Group 15 elements (e.g., Sb, Bi) and the like. Preferred metallic elements include transition metal elements (elements of Groups 3 to 12 of the Periodic Table of Elements). Among them, elements of the Groups 5 to 11 of the Periodic Table of Elements are preferred, of which Group 5 elements and Group 9 elements are typically preferred. Especially, Co, V or the like can advantageously be used. The valence of the metallic element is not particularly limited, and may range about from 1 to 6. The metallic elements have a valence of about 2 or 3 in many instances.

As the metallic compound (C1), there may be mentioned, for example, elementary substances, hydroxides, oxides (including complex oxides), halides (fluorides, chlorides, bromides, iodides), salts of oxoacids (e.g., nirates, sulfates, phosphates, borates, carbonates), oxoacids, isopolyacids, heteropolyacids, and other inorganic compounds of the aforementioned metallic elements; salts of organic acids (e.g., acetates, propionates, prussiates, naphthenates, stearates), complexes, and other organic compounds of the metallic elements. Ligands constituting the complexes include OH (hydroxo), alkoxy (e.g., methoxy, ethoxy, propoxy, butoxy), acyl (e.g., acetyl, propionyl), alkoxycarbonyl (e.g., methoxycarbonyl, ethoxycarbonyl), acetylacetonato, cyclopentadienyl group, halogen atoms (e.g., chlorine, bromine), CO, CN, oxygen atom, $H_2O$ (aquo), phosphine (triphenylphosphine and other triarylphosphines) and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Concrete examples of the metallic compound (C1) include, by taking cobalt compounds as example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; acetylacetonatocobalt, and other complexes, and other divalent or trivalent cobalt compounds. As illustrative vanadium compounds, there may be mentioned vanadium hydroxide, vanadium oxide, vanadium chloride, vanadyl chloride, vanadium sulfate, vanadyl sulfate, sodium vanadate, and other inorganic compounds; acetylacetonatovanadium, acetylacetonatovanadyl, and other complexes, and other vanadium compounds having a valence of 2 to 5. Examples of compounds of the other metallic elements include compounds corresponding to the above-mentioned cobalt or vanadium compounds. Each of the metallic compounds (C1) can be used singly or in combination.

The ratio of the metallic compound (C1) to the 1,2-dicarbonyl compound or its hydroxy reductant (A) is, for example, such that the former (C1)/the latter (A) (by mole) equals about 0 to 0.1, preferably about 0.001 to 0.05, and more preferably about 0.002 to 0.02.

Imide Compound (C2)

Of the substituents $R^1$ and $R^2$ in the imide compound (C2) represented by the formula (1), the halogen atom includes iodine, bromine, chlorine and fluorine. The alkyl group includes, for instance, methyl, ethyl, propyl, isopropyl, butyl, isobutyl, s-butyl, t-butyl, hexyl, decyl groups, and other straight- or branched-chain alkyl groups each having about 1 to 10 carbon atoms. As preferred alkyl groups, there may be mentioned, for instance, alkyl groups each having about 1 to 6 carbon atoms, and more preferably lower alkyl groups each having about 1 to 4 carbon atoms.

The aryl group includes phenyl, and naphthyl groups, for example; and the cycloalkyl group includes cyclopentyl, and cyclohexyl groups. As the alkoxy group, there maybe mentioned, for example, methoxy, ethoxy, isopropoxy, butoxy, t-butoxy, and hexyloxy groups, and other alkoxy groups each having about 1 to 6 carbon atoms, especially lower alkoxy groups each having about 1 to 4 carbon atoms.

Examples of the alkoxycarbonyl group include methoxycarbonyl, ethoxycarbonyl, isopropoxycarbonyl, butoxycarbonyl, t-butoxycarbonyl, and hexyloxycarbonyl groups, and other alkoxycarbonyl groups each having about 1 to 10 carbon atoms in the alkoxy moiety. Preferred alkoxycarbonyl groups include alkoxycarbonyl groups each having about 1 to 6 carbon atoms, and especially lower alkoxycarbonyl groups each having about 1 to 4 carbon atoms in the alkoxy moiety. As the illustrative acyl group, there may be mentioned formyl, acetyl, propionyl, butyryl, isobutyryl, valeryl, isovaleryl, and pivaloyl groups, and other acyl groups each having about 1 to 6 carbon atoms.

The substituents $R^1$ and $R^2$ may be identical to or different from each other. The $R^1$ and $R^1$ in the formula (1) may together form a double bond, or an aromatic or nonaromatic ring. The preferred aromatic or nonaromatic ring is a 5- to 12-membered ring, and especially a 6- to 10-membered ring. It may be a heterocyclic ring or condensed heterocyclic ring, but it is often a hydrocarbon ring. Such rings include, for example, nonaromatic alicyclic rings (e.g., cyclohexane ring and other cycloalkane rings which may have a substituent, cyclohexene ring and other cycloalkene rings which may have a substituent), nonaromatic bridged rings (e.g., 5-norbornene ring and other bridged hydrocarbon rings which may have a substituent), benzene ring, naphthalene ring and other aromatic rings (including condensed rings) which may have a substituent. The ring is composed of an aromatic ring in many instances. The ring may have a substituent such as an alkyl group, a haloalkyl group, a hydroxyl group, an alkoxy group, a carboxyl group, an alkoxycarbonyl group, an acyl group, a nitro group, a cyano group, an amino group, or a halogen atom.

In the formula (1) above, X represents an oxygen atom or a hydroxyl group, and the bond between the nitrogen atom N and X is a single bond or a double bond.

To $R^1$, $R^2$, or to the double bond or aromatic or nonaromatic ring formed together by $R^1$ and $R^2$, one or two N-substituted cyclic imido groups indicated in the formula (1) may be bonded. By way of illustration, when $R^1$ or $R^2$ is an alkyl group having 2 or more carbon atoms, the N-substituted cyclic imido group may be formed together with adjacent two carbon atoms constituting the alkyl group. Likewise, when $R^1$ and $R^2$ together form a double bond, the N-substituted cyclic imido group may be formed together with the double bond. In case that $R^1$ and $R^2$ together form an aromatic or nonaromatic ring, the N-substituted cyclic imido group may be formed with adjacent two carbon atoms constituting the aforementioned ring.

Preferred imide compounds (C2) include compounds represented by the following formulae:

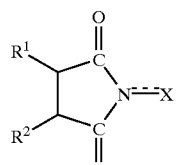
(1a)

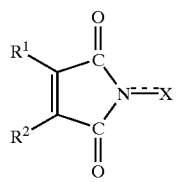
(1b)

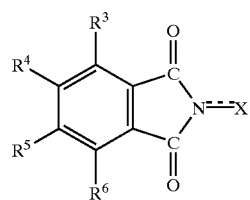
(1c)

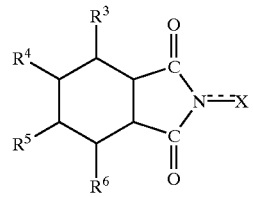
(1d)

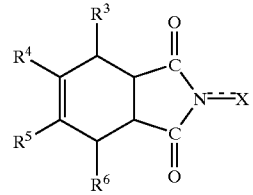
(1e)

(1f)

(wherein each of $R^3$ to $R^6$ is, identical to or different from each other, a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom; or, of $R^3$ to $R^6$, adjacent groups may together form an aromatic or nonaromatic ring; in the formula (1f), A represents a methylene group or an oxygen atom, and $R^1$ and $R^2$ have the same meanings as defined above; and one or two N-substituted cyclic imido groups indicated in the formula (1c) may be bonded to the benzene ring in the formula (1c) In the substituents $R^3$ to $R^6$, the alkyl group includes similar alkyl groups to those exemplified above, especially alkyl groups having about 1 to 6 carbon atoms. The haloalkyl group includes trifluoromethyl group and other haloalkyl groups each having about 1 to 4 carbon atoms, and the alkoxy group includes similar alkoxy groups to those mentioned above, and especially lower alkoxy groups each having about 1 to 4 carbon atoms. The alkoxycarbonyl group includes similar alkoxycarbonyl groups to those described above, particularly lower alkoxycarbonyl groups each having about 1 to 4 carbon atoms in the alkoxy moiety. As the acyl group, there may be mentioned similar acyl groups to those described above, especially acyl groups each having about 1 to 6 carbon atoms, and the illustrative halogen atoms include fluorine, chlorine and bromine atoms. The substituents $R^3$ to $R^6$ are each a hydrogen atom, a lower alkyl group having about 1 to 4 carbon atoms, a carboxyl group, a nitro group, or a halogen atom. The ring formed together by $R^3$ to $R^1$ includes similar rings to the aforementioned rings which are formed together by $R^1$ and $R^2$. Among them, aromatic or nonaromatic 5- to 12-membered rings are particularly preferred.

Each of the imide compounds (C2) represented by the formula (1) can be used singly or in combination.

Acid anhydrides corresponding to the imide compounds (C2) represented by the formula (1) include succinic anhydride, maleic anhydride and other saturated or unsaturated aliphatic dicarboxylic anhydrides, tetrahydrophthalic anhydride, hexahydrophthalic anhydride (1,2-cyclohexanedicarboxylic anhydride), 1,2,3,4- cyclohexanetetracarboxylic 1,2-dianhydride, and other saturated or unsaturated nonaromatic cyclic polycarboxylic anhydrides (alicyclic polycarboxylic anhydrides), HET anhydride (chlorendic anhydride), himic anhydride, and other bridged cyclic polycarboxylic anhydrides (alicyclic polycarboxylic anhydrides), phthalic anhydride, tetrabromophthalic anhydride, tetrachlorophthalic anhydride nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

As illustrative preferred imide compounds, there may be mentioned N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide. Among them, N-hydroxyimide compounds derived from alicyclic polycarboxylic anhydrides or aromatic polycarboxylic anhydrides are preferred, of which N-hydroxyphthalimide and other N-hydroxyimide compounds derived from aromatic polycarboxylic anhydrides are typically preferred.

The imide compounds (C2) can be prepared by a conventional imidation reaction, such as a process in which a corresponding acid anhydride is reacted with hydroxylamine, $NH_2OH$, and the acid anhydride group is ring-opened and then is ring-closed to give an imide.

The ratio of the imide compound (C2) to the 1,2-dicarbonyl compound or its hydroxy reductant (A) is, for example, such that the former (C2)/the latter (A) equals about 0 to 1, preferably about 0.001 to 0.5, and more preferably about 0.002 to 0.2.

The acylating agent of the invention has only to contain at least one compound selected from the metallic compound (C1) and the imide compound (C2). To be more specific, the embodiments of the acylating agent of the invention include; (i) an acylating agent composed of the 1,2-dicarbonyl compound or its hydroxy reductant (A), oxygen (B) and the metallic compound (C1), (ii) an acylating agent composed of the 1,2-dicarbonyl compound or its hydroxy reductant (A), oxygen (B) and the imide compound (C2), and (iii) an acylating agent composed of the 1,2-dicarbonyl compound or its hydroxy reductant (A), oxygen (B), the metallic compound (C1), and the imide compound (C2).

In many instances, the use of an acylating agent containing the metallic compound (C1) gives a high conversion rate, and the use of an acylating agent containing the imide compound (C2) yields an acyl group-containing compound with high selectivity. An acylating agent containing the imide compound (C2) has a feature that when used in combination with a hydroxy reductant of the 1,2-dicarbonyl compound as the compound (A), the hydroxy reductant is immediately converted into the corresponding 1,2-dicarbonyl compound in a system, and an acylation reaction proceeds smoothly.

The acylating agent of the invention may further comprise other ingredients including radical generators, and radical reaction accelerators than the ingredients (A), (B) and (C) Such additional ingredients include, for instance, halogens (e.g., chlorine, bromine), peracids (e.g., peracetic acid, m-chloroperbenzoic acid), and peroxides (e.g., hydrogen peroxide, hydroperoxide).

Acylation Method and Method for the Production of Acyl Group-containing Compounds According to the method of the invention, an organic substrate is reacted with the aforementioned acylating agent to form an acyl group-containing compound. The organic substrate includes a wide variety of compounds each having a carbon-hydrogen bond. Preferred organic substrates include compounds each having a methine carbon atom (or a tertiary carbon atom). As such compounds having a methine carbon atom, there may be mentioned (a) cyclic compounds each containing a methine group (i.e., a methine carbon-hydrogen bond) as a constitutive unit of the ring, and (b) chain compounds each having a methine carbon atom.

The cyclic compounds (a) include, for example, (a1) bridged cyclic compounds each having at least one methine group, and (a2) nonaromatic cyclic compounds (e.g., alicyclic hydrocarbons) each having a hydrocarbon group bonded to its ring. In this connection, the bridged cyclic compounds also include compounds in which two rings commonly possess two carbon atoms, such as hydrogenated compounds of condensed polycyclic aromatic hydrocarbons. Most of the cyclic compounds (a) are compounds belonging to terpenes.

As examples of the bridged cyclic compounds (a1), there may be mentioned decalin, bicyclo [2.2.0] hexane, bicyclo [2.2.2] octane, bicyclo [3.2.] octane, bicyclo [4.3.2] undecane, thujone, carane, pinane, pinene, bornane, bornylene, norbornane, norbornene, camphor, camphoric acid, camphene, tricyclene, tricyclo $[4.3.1.1^{2,5}]$ undecane, tricyclo $[5.2.1.0^{3,8}]$ decane, exotricyclo $[5.2.1.0^{2,6}]$ decane, endotricyclo $[5.2.1.0^{2,6}]$ decane, endotricyclo $[5.2.2.0^{2,6}]$ undecane, adamantane, 1-adamantanol, 1-chloroadamantane, 1-methyladamantane, 1,3-dimethyladamantane, 1-methoxyadamantane, 1-carboxyadamantane, 1-methoxycarbonyladamantane, 1-nitroadamantane, tetracyclo $[4.4.0.1^{2,5}.1^{7,10}]$ dodecane, perhydroacenaphthene, perhydroanthracene, perhydrofluorene, perhydrophenanthrene, perhydrophenalene, perhydroindene, quinuclidine, and other bridged cyclic hydrocarbons or bridged heterocyclic compounds each having 2 to 4 rings, and derivatives thereof. These bridged cyclic compounds each have a methine carbon atom at the bridgehead position (corresponding to a junction position when two rings commonly possess two atoms).

As the nonaromatic cyclic compound (a2) having a hydrocarbon group bonded to its ring, there may be mentioned 1-methylcyclopentane, 1-methylcyclohexane, limonene, mentene, menthol, carbomenthone, menthone, and other alicyclic hydrocarbons each having 3 to 15 members and their derivatives. The aforementioned hydrocarbons each have a hydrocarbon group (e.g., an alkyl group) bonded to its ring and having about to 20 (preferably 1 to 10) carbon atoms. The nonaromatic cyclic compound (a2) having a hydrocarbon group bonded to its ring has a methine carbon atom in a binding site between the ring and the hydrocarbon group.

The chain compound (b) having a methine carbon atom includes chain hydrocarbons each having a tertiary carbon atom, such as isobutane, isopentane, isohexane, 3-methylpentane, 2,3-dimethylbutane, 2-methylhexane, 3-methylhexane, 3,4-dimethylhexane, 3-methyloctane, and other aliphatic hydrocarbons each having about 4 to 20 (preferably 4 to 10) carbon atoms, and derivatives thereof.

In the method of the invention, the amount of the 1,2-dicarbonyl compound or its hydroxy reductant (A) is, for instance, equal to or more than about 1 mole (about 1 to 50 moles), preferably about 1.5 to 20 moles, and more preferably about 3 to 10 moles, per mole of the organic substrate. The 1,2-dicarbonyl compound or its hydroxy reductant (A) can be used as a reaction solvent, as well.

The proportion of the oxygen (B) is, usually per mole of the organic substrate, equal to or more than 0.5 mole (e.g., equal to or more than 1 mole), preferably about 1 to 100 moles, and more preferably about 2 to 50 moles. In many instances, an excess amount of molecular oxygen to the substrate is used.

The amount of the metallic compound (C1) is, for example, about 0.00001 to 1 mole, preferably about 0.0001 to 0.1 mole, and more preferably about 0.001 to 0.05 mole, per mole of the organic substrate. The proportion of the imide compound (C2) ranges, for instance, from about 0.00001 to 1 mole, preferably from about 0.001 to 0.7 mole, and more preferably from about 0.01 to 0.5 mole, per mole of the organic substrate.

The method of the invention is usually performed in an organic solvent. The organic solvent includes, for example, acetic acid, propionic acid, and other organic acids; acetonitrile, propionitrile, benzonitrile, and other nitrites; formamide, acetamide, dimethylformamide (DMF), dimethylacetamide, and other amides; t-butanol, t-amyl alcohol, and other alcohols; hexane, octane, and other aliphatic hydrocarbons; benzene, toluene, and other aromatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; diethyl ether, diisopropyl ether, and other ethers; and mixtures of these solvents. As the solvent, acetic acid or another organic acid, benzonitrile or another nitrite, trifluoromethylbenzene or another halogenated hydrocarbon is frequently employed.

According to the method of the invention, an acylation reaction proceeds even under comparatively mild conditions. The react on temperature can adequately be selected according to, for instance, the species of the organic substrate, and is about 0 to 300° C., preferably about 30 to 250° C., and more preferably about 40 to 200° C., for instance. The reaction is frequently performed at about 40 to 150° C. The reaction can be carried out at ambient pressure or under pressure. When the reaction is conducted under pressure, the pressure is usually about 1 to 100 atm (e.g. 1.5 to 80 atm), preferably about 2 to 70 atm. The reaction time can adequately be selected within the range of, for example, 30 minutes to 48 hours according to the reaction temperature and pressure.

The reaction can be performed in a batch system, semi-batch system, continuous system or another conventional system, in the presence of oxygen or under flow of oxygen. After the completion of the reaction, reaction products can be isolated and purified with facility in a conventional manner including, for example, filtration, concentration, distillation, extraction, crystallization, recrystallization, column chromatography and other isolation means, or any combination of these isolation means.

With he use of the acylating agent, probably because the reaction proceeds via a radical mechanism, an acyl group corresponding to the 1,2-dicarbonyl compound (e.g., a $R^aCO$ group or $R^bCO$ group when a 1,2-dicarbonyl compound or its hydroxy reductant represented by the formula (2) is used) can be introduced even to a carbon atom which is not activated by, for example, a carbonyl group. Thus, an acyl group-containing compound can be obtained in satisfactory yield. Especially, from a compound having a methine carbon atom, an acyl group-containing compound having an acyl group introduced to the methine carbon can be obtained in high yield. For example, when adamantane or another bridged cyclic hydrocarbon (a1) is acylated, an acyl group-containing compound having an acyl group introduced to the bridgehead position can be obtained. In addition, acylation of isobutane or another chain compound (b) having a methine carbon atom can yield t-butyl ketone or another t-alkyl ketone.

Production of Adamantane Derivatives

Different types of adamantane derivatives can be produced by the use of the above-mentioned acylation method or the method for the production of acyl group-containing compounds.

By way of illustration, the reaction of the adamantane derivative represented by the formula (3) with the acylating agent can give the adamantane derivative represented by the formula (4).

The halogen atom in $R^{c1}$, $R^{d1}$, and $R^{e1}$ in the formula (3) includes, for instance, fluorine, chlorine and bromine atoms. As the alkyl group, there may be mentioned methyl, ethyl, propyl, isopropyl, butyl, isobutyl, s-butyl, t-butyl, pentyl, hexyl, octyl, and decyl groups, and other alkyl groups each having about 1 to 10 carbon atoms, preferably about 1 to 6 carbon atoms, and more preferably about 1 to 4 carbon atoms. The typically preferred alkyl groups are methyl group and ethyl group, of which methyl group is desirable.

The protective group for hydroxyl group and hydroxymethyl group in $R^{c1}$, $R^{d1}$, and $R^{e1}$ includes a conventional protective group such as an alkyl group (e.g., methyl, or t-butyl group, or another $C_{1-4}$ alkyl group), an alkenyl group (e.g., allyl group), a cycloalkyl group (e.g., cyclohexyl group), an aryl group (e.g., 2,4-dinitrophenyl group), an aralkyl group (e.g., benzyl, 2,6-dichlorobenzyl, 3-bromobenzyl, 2-nitrobenzyl, or triphenylmethyl group), a substituted methyl group (e.g., methoxymethyl, methylthiomethyl, benzyloxymethyl, t-butoxymethyl, 2-methoxyethoxymethyl, 2,2,2-trichloroethoxymethyl, bis (2-chloroethoxy)methyl, or 2-(trimethylsilyl)ethoxymethyl group), a substituted ethyl group (e.g., 1-ethoxyethyl, 1-methyl-l-methoxyethyl, 1-isopropoxyethyl, or 2,2,2-trichloroethyl group), a tetrahydropyranyl group, a tetrahydrofuranyl group, an acyl group (e.g., formyl, acetyl, proplonyl, butyryl, isobutyryl, valeryl, pivaloyl, or another $C_{1-6}$ aliphatic acyl group; acetoacetyl group; benzoyl, or naphthoyl group, or another aromatic acyl group), an alkoxycarbonyl group (e.g., methoxycarbonyl, ethoxycarbonyl, or t-butoxycarbonyl group, or another $C_{1-4}$ alkoxy-carbonyl group), an aralkyloxycarbonyl group (e.g., benzyloxycarbonyl group, p-methoxybenzyloxycarbonyl group), a substituted or unsubstituted carbamoyl group (e.g., carbamoyl, methylcarbamoyl, or phenylcarbamoyl group), a dialkylphosphinothloyl group (e.g., dimethylphosphinothioyl group), a diarylphophinothioyl group (e.g., diphenylphosphinothioyl group), a substituted silyl group (e.g., trimethylsilyl, t-butyldimethylsilyl, tribenzylsilyl, or triphenylsilyl group). In addition, when two or more hydroxyl groups (including hydroxymethyl groups) are present in the molecule, a divalent hydrocarbon group (e.g., methylene, ethylidene, isopropylidene, cyclopentylidene, cyclohexylidene, or benzylidene group) which may have a substituent can be used as the protective group. The preferred protective group for hydroxyl group includes a $C_{1-4}$ alkyl group, a substituted methyl group, a substituted ethyl group, an acyl group, a $C_{1-4}$ alkoxy-carbonyl group, a substituted or unsubstituted carbamoyl group, or a divalent hydrocarbon group which may have a substituent.

The protective group for amino group in $R^{c1}$, $R^{d1}$, and $R^{e1}$ includes the aforementioned alkyl group, aralkyl group, acyl group, alkoxycarbonyl group, aralkyloxycarbonyl group, dialkylphosphinothioyl group, and diarylphosphinothioyl group exemplified as the protective group for hydroxyl group. A $C_{1-4}$ alkyl group, a $C_{2-6}$ aliphatic acyl group, an aromatic acyl group, or a $C_{1-4}$ alkoxy-carbonyl group is desirably used as the protective group for amino group.

As the protective group for carboxyl group in $R^{c1}$, $R^{d1}$, and $R^{e1}$, use is made of, for instance, an alkoxy group (e.g., methoxy, ethoxy, butoxy or another $C_{1-6}$ alkoxy group), a cycloalkyloxy group, an aryloxy group (e.g., phenoxy group), an aralkyloxy group (e.g., benzyloxy group), a trialkylsilyloxy group (e.g., trimethylsilyloxy group), an amino group which may have a substituent (e.g., amino group; methylamino group, dimethylamino group or another mono- or di-$C_{1-6}$ alkyl-substituted amino group), a hydrazino group, an alkoxycarbonylhydrazino group, or an aralkyloxycarbonylhydrazino group. The preferred protective group for carboxyl group includes a $C_{1-6}$ alkoxy group (especially, $C_{1-4}$ alkoxy group), a mono- or di-$C_{1-6}$ alkyl-substituted amino group (especially, a mono- or di-$C_{1-4}$ alkyl-substituted amino group).

The acyl groups in $R^{c1}$, $R^{d1}$, and $R^{e1}$ include acyl groups corresponding to the 1,2-dicarbonyl compounds, such as acyl groups corresponding to the $R^a CO$ group or $R^b CO$ group. The preferred acyl groups include $C_{2-5}$ saturated aliphatic acyl groups, cycloalkylcarbonyl groups, and arylcarbonyl groups, of which an acetyl group and propionyl group are desirable. Among them, an acetyl group is typically preferred.

In the compounds represented by the formula (3) [as well as in the compounds represented by the formula (4), (4a), (5), (6), and (7)], of carbon atoms constituting the adamantane skeleton, the other carbon atoms (carbon atoms constituting methylene groups in the formula) than those at the bridgehead positions may have a substituent. Such substituents include an oxo group, an alkyl group (e.g., methyl group or another $C_{1-4}$ alkyl group), an acyl group (e.g., acetyl group or another $C_{2-5}$ aliphatic acyl group, benzoyl group or another arylcarbonyl group), a hydroxyl group, an alkoxy group (e.g., methoxy group or another $C_{1-4}$ alkoxy group), an acyloxy group (e.g., acetoxy or another $C_{2-6}$ aliphatic acyloxy group, benzoyloxy group, or another arylcarbonyloxy group), a carboxyl group, an alkoxycarbonyl group (methoxycarbonyl, or ethoxycarbonyl group or another $C_{1-4}$ alkoxy-carbonyl group), a halogen atom (e.g., fluorine, chlorine, or bromine atom), or a cyano group.

The compounds represented by the formula (3) can be produced according to a known technique. By way of illustration, an adamantane derivative having a hydroxyl group at the bridgehead position can be obtained by oxidizing an adamantane derivative having a hydrogen atom at the bridgehead position with oxygen in the presence of a catalyst composed of the imide compound represented by the formula (1), or a catalyst composed of the aforementioned catalyst and the metallic compound (c1). The amount of the imide compound is, for example, about 0.001 to 1 mole per mole of the adamantane derivative having a hydrogen atom at the bridgehead position; and the proportion of the metallic compound (c1) is, for instance, about 0.0001 to 0.7 mole per mole of the adamantane derivative having a hydrogen atom at the bridgehead position. The oxygen is generally used in excess moles to the adamantane derivative having a hydrogen atom at the bridgehead position. As the oxygen, molecular oxygen can be used. The reaction is carried out, for example, in a solvent such as acetic acid or another organic acid, or acetonitrile, benzonitrile, or another nitrile, at ambient pressure or under pressure at a temperature of about 0 to 300° C. (preferably 30 to 250° C.) Likewise, an adamantane derivative having a carboxyl group at the bridgehead position can be obtained by allowing an adamantane derivative having a hydrogen atom at the bridgehead position to contact with carbon monoxide and oxygen, in the presence of a catalyst composed of the imide compound represented by the formula (1), or a catalyst composed of the aforementioned catalyst and the metallic compound (c1). The amounts of the imide compound and metallic compound (c1) are similar to those in the aforementioned oxidation reaction. The amount of carbon monoxide is, usually, equal to or more than 1 mole (e.g., 1 to 100 moles) per mole of the adamantane derivative having a hydrogen atom at the bridgehead position. The proportion of the oxygen is, for instance, equal to or more than 0.5 mole (e.g., 0.5 to 100 moles) per mole of the adamantane derivative having a hydrogen atom at the bridgehead position. The ratio of carbon monoxide to the oxygen is such that carbon monoxide: oxygen (by mole) equals about 1:99 to 99:1, preferably about 10:99 to 99:1. The reaction is carried out, for example, in a solvent such as acetic acid or another organic acid, or acetonitrile, benzonitrile, or another nitrile, at ambient pressure or under pressure at a temperature of about 0 to 200° C. (preferably 10 to 150° C.)

An adamantane derivative having a hydroxymethyl at the bridgehead position can be obtained by reducing the above-mentioned adamantane derivative having a carboxyl group at the bridgehead position according to a conventional reduction process using a reducing agent (e.g., a hydrogen-platinum group metal catalyst, a sodium borohydride-Lewis acid, lithium aluminium hydride, diborane).

An adamantane derivative having a nitro group at the bridgehead position can be obtained by allowing an adamantane derivative having a hydrogen atom at the bridgehead position to contact with a nitrogen oxide (e.g., $N_2O_3$, $N_2O—O_2$, $NO—O_2$, $NO_2$) in the presence of, or in the absence of, a catalyst composed of the imide compound represented by the formula (1). The amount of the imide compound is similar to that in the oxidation reaction. The proportion of the nitrogen oxide is generally about 1 to 50 moles, and preferably about 1.5 to 30 moles per mole of the adamantane derivative having a hydrogen atom at the bridgehead position. The reaction is performed, for example, in a solvent such as acetic acid or another organic acid, or acetonitrile, benzonitrile or another nitrile, at atmospheric pressure or under pressure at a temperature of about 0 to 150° C. (preferably 10 to 125° C.).

By reducing the aforementioned adamantane derivative having a nitro group at the bridgehead position according to a conventional reduction process using a reducing agent [e.g., a hydrogen-metal catalyst (e.g., a platinum group metal, nickel, copper chromite), sodium borohydride, diborane], an adamantane derivative having an amino group at the bridgehead position can be obtained.

Furthermore, the protective group can be introduced and eliminated in a conventional manner. In this connection, a compound having an acyl group can be prepared by the use of the method of the invention.

Examples of the compounds represented by the formula (3) include adamantane, 1-methyladamantane, 1-ethyladamantane, 1,3-dimethyladamantane, 1-adamantanol, 1,3-adamantanediol, 1-methoxyadamantane, 1-acetoxyadamantane, 1-hydroxymethyladamantane, 1-aminoadamantane, 1-acetylaminoadamantane, 1-benzoylaminoadamantane, 1-carboxyadamantane, 1-ethoxycarbonyladamantane, 1-nitroadamantane, and 1-acetyladamantane.

As the acyl group represented by R in the formula (4), there may be mentioned an acyl group corresponding to the 1,2-dicarbonyl compound, such as an acyl group corresponding to the $R^aCO$ group or $R^bCO$ group. The preferred acyl groups include, for instance, $C_{2-5}$ saturated aliphatic acyl groups, cycloalkylcarbonyl groups, and arylcarbonyl groups, of which acetyl group and propionyl group, in especial acetyl group, are typically preferred. As the alkyl groups; the protective groups for the hydroxyl group, hydroxymethyl group, amino groups and carboxyl groups; and the acyl groups in the $R^{c2}$, $R^{d2}$, and $R^{e2}$, similar groups to the alkyl groups and the like in $R^{c1}$, $R^{d1}$, and $R^{e1}$ may be mentioned. In this connection, when $R^{c1}$, $R^{d1}$, or $R^{e1}$ is a hydrogen atom, it can be converted to an acyl group or a hydroxyl group by the reaction. In some cases depending on conditions, an oxo group may be introduced to a methylene group adjacent to the bridgehead position of the adamantane skeleton.

Of the compounds represented by the formula (4), the adamantane derivatives represented by the formula (7) are novel compounds. The acyl groups represented by R and $R^{c5}$, the alkyl groups represented by $R^{d5}$ and $R^{e5}$, the protective groups for the hydroxyl group and the like, and the acyl groups include similar groups to those in R, $R^{c1}$, $R^{d1}$, and $R^{e1}$ in the compounds of the formula (3) or of the formula (4).

The concrete examples of the compounds represented by the formula (7) are 1-acetyl-3-adamantanol, 1,3-diacetyladamantane, 1-acetyl-2-oxo-3-adamantanol, 1,3-diacetyl-5-adamantanol, 1-acetyl-3,5-adamantanediol, -acetyl-3-methyl-5-adamantanol, 1-acetyl-3,5-dimethyl-7 -adamantanol, 1,3-diacetyl-5,7-dimethyladamantane, 1-acetyl-3-methoxy-5-adamantanol, 1-acetoxy-3-acetyl-5-adamantanol, 1-acetyl-3-hydroxymethyl-5-adamantanol, 1-acetyl-3-amino-5-adamantanol, 1-acetyl-3-acetylamino-5-adamantanol, 1-acetyl-3-benzoylamino-5-adamantanol, 1-acetyl-3-carboxy-5-adamantanol, 1-acetyl-3-ethoxycarbonyl-5-adamantanol, and 1-acetyl-3-nitro-5-adamantanol.

Production of Tricyclo [$5.2.1.0^{2,6}$] Decane Derivatives

A variety of tricyclo [$5.2.1.0^{2,6}$] decane derivatives can be produced with the use of the acylation method or the method for the production of acyl group-containing compounds. For instance, the reaction of a tricyclo [$5.2.1.0^{2,6}$] decane derivative represented by the formula (11) with the acylating agent can yield a tricyclo [$5.2.1.0^{2,6}$] decane derivative represented by the formula (12). In this connection, the tricyclo [$5.2.1.0^{2,6}$] decane derivatives include endo-isomers and exo-isomers.

The halogen atoms; the alkyl groups; the protective groups for hydroxyl group, hydroxymethyl group, amino group and carboxyl group; acyl groups; and preferable groups of these groups in $R^{p1}$, $R^{q1}$, $R^{r1}$, and $R^{s1}$ in the formula (11) may be exemplified by similar groups to those in $R^{c1}$, $R^{d1}$, and $R^{e1}$ in the formula (3).

In the compounds represented by the formula (11) [as well as in the compounds represented by the formula (12)], the other carbon atoms (carbon atoms constituting methylene groups in the formula) than those at the bridgehead positions of carbon atoms constituting the tricyclodecane skeleton may have a substituent. The substituent just mentioned above includes an oxo group, an alkyl group (e.g., methyl group or another $C_{1-4}$ alkyl group), an acyl group (e.g., acetyl group or another $C_{2-5}$ aliphatic acyl group, benzoyl group or another arylcarbonyl group), a hydroxyl group, an alkoxy group (e.g., methoxy group or another $C_{2-6}$ alkoxy group), an acyloxy group (e.g., acetoxy or another $C_{2-6}$ aliphatic acyloxy group, benzoyloxy group or another arylcarbonyloxy group), a carboxyl group, an alkoxycarbonyl group (methoxycarbonyl, or ethoxycarbonyl group or another $C_{1-4}$ alkoxy-carbonyl group), a halogen atom (e.g., fluorine, chlorine, or bromine atom), or a cyano group.

The compounds represented by the formula (11) can be obtained, for example, from tricyclo [$5.2.1.0^{2,6}$] decane derivatives having a hydrogen atom at the bridgehead position in a similar manner to the method described on the adamantane compounds represented by the formula (3). In this connection, the acyl group-containing compounds can be produced by the use of the method of the invention.

As examples of the compounds represented by the formula (11), there may be mentioned tricyclo [$5.2.1.0^{2,6}$] decane, 1-methyltricyclo [$5.2.1.0^{2,6}$] decane, 1-ethyltricyclo [$5.2.1.0^{2,6}$] decane, 1,7-dimethyltricyclo [$5.2.1.0^{2,6}$] decane, 2-methyltricyclo [$5.2.1.0^{2,6}$] decane, 1 -hydroxytricyclo [$5.2.1.0^{2,6}$] decane, 2-hydroxytricyclo [$5.2.1.0^{2,6}$] decane, 1,7-dihydroxytricyclo [$5.2.1.0^{2,6}$] decane, 1-methoxytricyclo [$5.2.1.0^{2,6}$] decane, 2-methoxytricyclo [$5.2.1.02^{2,6}$] decane, 1-acetoxytricyclo [$5.2.1.0^{2,6}$] decane, 2-acetoxytricyclo [$5.2.1.0^{2,6}$] decane, 1-hydroxymethyltricyclo [$5.2.1.0^{2,6}$] decane, 2-hydroxymethyltricyclo [$5.2.1.0^{2,6}$] decane, 1-aminotricyclo [$5.2.1.0^{2,6}$] decane, 2-aminotricyclo [$5.2.1.0^{2,6}$] decane, 1-acetylaminotricyclo [$5.2.1.0^{2,6}$] decane, 2-acetylaminotricyclo [$5.2.1.0^{2,6}$] decane, 1-benzoylaminotricyclo [$5.2.1.0^{2,6}$] decane, 2-benzoylaminotricyclo [$5.2.1.0^{2,6}$] decane, 1-carboxytricyclo [$5.2.1.0^{2,6}$] decane, 2-carboxytricyclo [$5.2.1.0^{2,6}$] decane, 1-ethoxycarbonyltricyclo [$5.2.1.0^{2,6}$] decane, 2-ethoxycarbonyltricyclo [$5.2.1.0^{2,6}$] decane, 1-nitrotricyclo [$5.2.1.0^{2,6}$] decane, 2-nitrotricyclo [$5.2.1.0^{2,6}$] decane, 1-acetyltricyclo [$5.2.1.0^{2,6}$] decane, and 2-acetyltricyclo [$5.2.1.0^{2,6}$] decane. These compounds include endo-isomers and exc-isomers.

The acyl groups in $R^{p2}$, $R^{q2}$, $R^{r2}$, and $R^{s2}$ in the formula (12) include acyl groups corresponding to the 1,2-dicarbonyl compounds, such as acyl groups corresponding to the aforementioned $R^aCO$ group or $R^bCO$ group. The preferred acyl groups include $C_{2-5}$ saturated aliphatic acyl groups, cycloalkylcarbonyl groups, and arylcarbonyl groups, of which an acetyl group and propionyl group are desirable. Among them, an acetyl group is typically preferred. As the alkyl groups; the protective groups for the hydroxyl group, hydroxymethyl group, amino group and carboxyl group; and the acyl groups in $R^{p2}$, $R^{q2}$, and $R^{s2}$, similar groups to the alkyl groups and the like in $R^{c1}$, $R^{d1}$, and $R^{e1}$ may be mentioned. In this connection, when $R^{p1}$, $R^{q1}$, $R^{r1}$, or $R^{s1}$ is a hydrogen atom, it can be converted to a hydroxyl group by the reaction. In some cases depending on conditions, an oxo group may be introduced to a methylene group adjacent to the bridgehead position of the tricyclodecane skeleton.

The compounds represented by the formula (12) are novel compounds. Concrete examples of the compounds represented by the formula (12) include 2-acetyltricyclo [$5.2.1.0^{2,6}$] decane, 2,6-diacetyltricyclo [$5.2.1.0^{2,6}$] decane, 2-acetyl-7-methyltricyclo [$5.2.1.0^{2,6}$] decane, 2-acetyl-7-ethyltricyclo [$5.2.1.0^{2,6}$] decane, 2-acetyl-1,7-dimethyltricyclo [$5.2.1.0^{2,6}$] decane, 2-acetyl-7-hydroxytricyclo [$5.2.1.0^{2,6}$] decane, 2-acetyl-1,7- dihydroxytricyclo [5.2.1.0$^{2,6}$] decane, 2-acetyl-7-methoxytricyclo [5.2.1.0$^{2,6}$] decane, 2-acetyl-6-methoxytricyclo [5.2.1.0$^{2,6}$] decane, 2-acetoxy-6 acetyltricyclo [5.2.1.0$^{2,6}$] decane, 2-acetyl-7-hydroxymethyltricyclo [5.2.1.0$^{2,6}$] decane, 2-acetyl-6-hydroxymethyltricyclo [5.2.1.0$^{2,6}$] decane, 2-acetyl-7-aminotricyclo [5.2.1.0$^{2,6}$] decane, 2-acetyl-6-aminotricyclo [5.2.1.0$^{2,6}$] decane, 2-acetyl-7-acetylaminotricyclo [5.2.1.0$^{2,6}$] decane, 2-acetyl-6-acetylaminctricyclo [5.2.1.0$^{2,6}$] decane, 2-acetyl-7-benzoylaminotricyclo [5.2.1.0$^{2,6}$] decane, 2-acetyl-6-benzoylaminotricyclo [5.2.1.0$^{2,6}$] decane, 2-acetyl-7-carboxytricyclo [5.2.1.0$^{2,6}$] decane, 2-acetyl-6-carboxytricyclo [5.2.1.0$^{2,6}$] decane, 2-acetyl-7-ethoxycarbonyltricyclo [5.2.1.0$^{2,6}$] decane, 2-acetyl-6-ethoxycarbonyltricyclo [5.2.1.0$^{2,6}$] decane, 2-acetyl-7-nitrotricyclo [5.2.1.0$^{2,6}$] decane, and 2-acetyl-6-nitrotricyclo [5.2.1.0$^{2,6}$] decane. These compounds include endo-isomers and exo-isomers.

Production of Decalin Derivatives

Furthermore, different kinds of decalin derivatives each having an acyl group can be produced by using the above acylation method or the method for the production of acyl group-containing compounds. For example, the decalin derivatives represented by the formula (14) can be obtained by reacting the decalin derivatives represented by the formula (13) with the acylating agent. Such decalin derivatives include cis-isomers and trans-isomers.

As the halogen atoms; alkyl groups; the protective groups for hydroxyl group, hydroxymethyl group, amino group and carboxyl group; the acyl groups; and preferred groups of these groups in $R^{r1}$ and $R^{u1}$ in the formula (13) may be exemplified by similar groups to those in $R^{c1}$, $R^{d1}$, and $R^{e1}$ in the formula (3).

In the compounds represented by the formula (13) [as well as in the compounds represented by the formula (14)], the other carbon atoms (carbon atoms constituting methylene groups in the formula) than those at the bridgehead positions of carbon atoms constituting the decalin skeleton may have a substituent. The substituent just mentioned above includes an oxo group, an alkyl group (e.g., methyl group or another $C_{1-4}$ alkyl group) an acyl group (e.g., acetyl group or another $C_{2-5}$ aliphatic acyl group, benzoyl group or another arylcarbonyl group), a hydroxyl group, an alkoxy group (e.g., methoxy group or another $C_{1-4}$ alkoxy group), an acyloxy group (e.g., acetoxy or another $C_{2-6}$ aliphatic acyloxy group, benzoyloxy group or another arylcarbonyloxy group), a carboxyl group, an alkoxycarbonyl group (methoxycarbonyl or ethoxycarbonyl group, or another $C_{1-4}$ alkoxy-carbonyl group), a halogen atom (e.g., fluorine, chlorine, or bromine atom), or a cyano group.

The compounds represented by the formula (13) can be produced from decalin derivatives having a hydrogen atom at the bridgehead position according to a similar manner to the method described for the adamantane derivatives represented by the formula (3). In this connection, acyl group-containing compounds can be produced by the use of the method of the invention.

The illustrative compounds represented by the formula (13) include decalin, 4a-methyldecalin, 4a-ethyldecalin, 4a-hydroxydecalin, 4a-methoxydecalin, 4a-acetoxydecalin, 4a-hydroxymethyldecalin, 4a-aminodecalin, 4a-acetylaminodecalin, 4a-benzoylaminodecalin, 4a-carboxydecalin, 4a-ethoxycarbonyldecalin, 4a-nitrodecalin, and 4a-acetyldecalin. These compounds include cis-isomers and trans-isomers.

The acyl groups in $R^{r2}$ and $R^{u2}$ in the formula (14) include acyl groups corresponding to the 1,2-dicarbonyl compounds, such as acyl groups corresponding to the aforementioned $R^aCO$ group or $R^bCO$ group. The preferred acyl groups include $C_{2-5}$ saturated aliphatic acyl groups, cycloalkylcarbonyl groups, and arylcarbonyl groups, of which an acetyl group and propionyl group are desirable. Among them, an acetyl group is typically preferred. As the alkyl groups; the protective groups for the hydroxyl group, hydroxymethyl group, amino group and carboxyl group; and the acyl groups in $R^{r2}$ and $R^{u2}$, similar groups to the alkyl groups and the like in $R^{c1}$, $R^{d1}$, and $R^{e1}$ may be mentioned. In this connection, when $R^{r1}$ or $R^{u1}$ is a hydrogen atom, it may be converted to a hydroxyl group by the reaction. In some cases depending on conditions, an oxo group may be introduced to a methylene group adjacent to the bridgehead position of the decalin skeleton.

The compounds represented by the formula (14) are novel compounds. As practical examples of the compounds represented by the formula (14), there may be mentioned 4a-acetyldecalin, 4a-acetyl-8a-methyldecalin, 4a-acetyl-8a-ethyldecalin, 4a-acetyl-8a-hydroxydecalin, 4a-acetyl-8a-methoxydecalin, 4a-acetoxy-8a-acetyldecalin, 4a-acetyl-8a-hydroxymethyldecalin, 4a-acetyl-8a-aminodecalin, 4a-acetyl-8a-acetylaminodecalin, 4a-acetyl-8a-benzoylaminodecalin, 4a-acetyl-8a-carboxydecalin, 4a-acetyl-8a-ethoxycarbonyldecalin, 4a-acetyl-8a-nitrodecalin, and 4a, 8a-diacetyldecalin. These compounds include cis-isomers and trans-isomers.

Production of Vinyl Group-containing Polycyclic Compounds

Polycyclic compounds each containing a vinyl group which may have a substituent can be prepared by the use of the acylation method or the method for the production of acyl group-containing compounds of the invention.

To be more specific, the compounds represented by the formula (18) are obtained by: reacting a polycyclic compound represented by the formula (15) with the acylating agent composed of (A1) the 1,2-dicarbonyl compound represented by the formula (2b) or its hydroxy reductant, (B) oxygen, and (C) at least one compound selected from (C1) the metallic compound and (C2) the imide compound represented by the formula (1) to give a compound represented by the formula (16), reducing the obtained compound represented by the formula (16) to give a compound represented by the formula (17), and subjecting it to dehydration reaction.

The polycyclic compounds represented by the formula (15) include, for instance, the aforementioned bridged cyclic compounds (a1). As the polycyclic compounds, the adamantane derivatives represented by the formula (3), the tricyclo [5.2.1.0$^{2,6}$] decane derivatives represented by the formula (11), and the decalin derivatives represented by the formula (13) are typically preferred.

The hydrocarbon groups and heterocyclic groups in $R^b$, $R^f$, and $R^g$ in the formula (2b) include groups similar to the hydrocarbon groups and heterocyclic groups in the substituent $R^a$, for example. Preferred substituent $R^b$ and group —CH ($R^f$) ($R^g$) are each an alkyl group having 1 to 4 carbon atoms (methyl, ethyl, propyl, isopropyl, butyl, isobutyl or s-butyl group), and more Preferably methyl group or ethyl group, and in particular methyl group.

The compounds represented by the formula (15) can be acylated according to the aforementioned method of the invention. The compounds represented by the formula (16)

can be reduced by, for instance, a reduction process with a metal hydride complex compound such as lithium aluminium hydride or sodium borohydride; a reduction process using borane; or a catalytic reduction process using a Rh catalyst. The reduction may be carried out in a solvent at a temperature of from about −100° C. to about 150° C. The solvent can be selected, in accordance with the reduction process, from diethyl ether, tetrahydrofuran and other ethers; hexane and other aliphatic hydrocarbons; cyclohexane and other alicyclic hydrocarbons; toluene and other aromatic hydrocarbons; ethanol and other alcohols; acetic acid and other carboxylic acids; methylene chloride and other halogenated hydrocarbons; and the like. The dehydration reaction of the compounds represented by the formula (17) can be conduced in an appropriate solvent (for instance, any of the above exemplified solvents) at a temperature of from about 0° C. to about 150° C., where necessary in the presence of sulfuric acid or another acid or a dehydrating agent. The dehydration reaction may be carried out while distilling off by-produced water through azeotropic distillation.

The production of vinyl group-containing adamantane derivatives will now be described in more detail as typical example. As shown in the following reaction process chart, an adamantane derivative represented by the formula (3) as a starting material is subjected to the acylation reaction to give an acyl group-containing adamantane derivative represented by the formula (4a). The compound represented by the formula (4a) is then reduced to give an alcohol represented by the formula (5), and this alcohol is subjected to dehydration reaction to give a vinyl group-containing adamantane derivative represented by the formula (6).

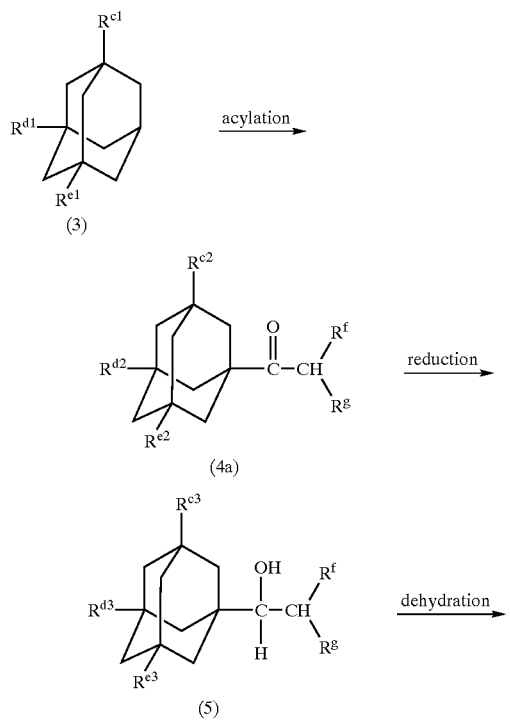

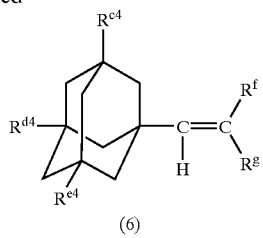

In the above reaction process chart, each of $R^{c2}$, $R^{d2}$, and $R^{e2}$ in the formula (4a) is, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, or an acyl group, and $R^f$ and $R^g$ have the same meanings as defined above. Each of $R^{c3}$, $R^{d3}$, and $R^{e3}$ in the formula (5), identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, an acyl group, or a hydroxylmethyl group which may have a substituent; and $R^f$ and $R^g$ have the same meanings as defined above. Each of $R^{c4}$, $R^{d4}$, and $R^4$ in the formula (6) is, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, an acyl group, a hydroxylmethyl group which may have a substituent, or a vinyl group which may have a substituent; and $R^f$ and $R^g$ have the same meanings as defined above.

As the halogen atoms, alkyl groups, protective groups for hydroxyl group or the like, and acyl groups in $R^{c2}$, $R^{d2}$, $R^{e2}$, $R^{c3}$, $R^{d3}$, $R^{e3}$, $R^{c4}$, $R^{d4}$, and $R^{e4}$, similar groups to those in the $R^{c1}$, $R^{d1}$, and $R^{e1}$ above are mentioned. The "hydroxymethyl group which may have a substituent" in $R^{c3}$, $R^{d3}$, $R^{e3}$, $R^{c4}$, $R^{d4}$, and $R^{e4}$ means a functional group formed by reducing the acyl group through the reduction reaction. Furthermore, the "vinyl group which may have a substituent" in $R^{c4}$, $R^{d4}$, and $R^{e4}$ means a functional group formed by dehydrating the hydroxymethyl group which may have a substituent through the dehydration reaction.

Thus obtained polycyclic compounds such as adamantane derivatives each containing a vinyl group which may have a substituent are useful as monomeric components for functional polymers.

The compounds represented by the formula (4a) can be induced, as shown in the following reaction process chart, to an adamantane derivative (8) having a vinyl group with a halogen atom substituted on the α-position, or to an adamantane derivative (10) having a vinyl group with a cyano group substituted on the α-position.

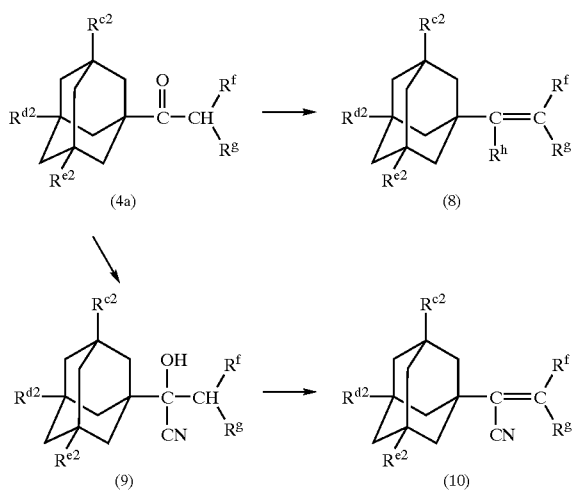

In the above chart, $R^{c2}$, $R^{d2}$, $R^{e2}$, $R^f$, and $R^g$ have the same meanings as defined above; and $R^h$ is a halogen atom (e.g., chlorine or bromine atom).

To be more specific, the adamantane derivative (8) having a vinyl group with a halogen atom substituted on its α-position can be obtained by reacting the compound represented by the formula (4a) with thionyl chloride or another halogenating agent, where necessary in the presence of pyridine, triethylamine or another base. The reaction can be carried out in the presence of, or in the absence of, an appropriate solvent (for instance, any of the solvents mentioned above) at a temperature of from about 0° C. to about 150° C. Likewise, the adamantane derivative (10) having a vinyl group with a cyano group substituted on its α-position can be obtained by, α-owing trimethylsilyl cyanide or another cyanidation agent to act on the compound represented by the formula (4a), and where necessary treating the product with an acid (e.g., hydrochloric acid) or the like to give a corresponding cyanhydrin (9), and subjecting this compound to dehydration reaction. The reaction of the compound represented by the formula (4a) with the cyanidation agent may be carried out in an appropriate solvent (e.g., any of the aforementioned solvents) at a temperature of from about 0° C. to about 150° C., where necessary in the presence of zinc iodide or another Lewis acid. The dehydration reaction of the cyanhydrin (9) can be performed, for instance, in a solvent such as pyridine, at a temperature of from about 0° C. to about 200° C., where necessary by allowing phosphorus oxychloride or another dehydrating agent to act on the cyanhydrin.

The thus obtained adamantane derivatives each represented by the formula (8) or (10) are also useful as monomeric components of functional polymers.

Production of Epoxy Group-containing Polycyclic Compounds

By reacting the vinyl group-containing polycyclic compounds represented by the formula (18) (e.g., adamantane derivatives, tricyclo [5.2.1.0$^{2,6}$] decane derivatives, decalin derivatives and other bridged cyclic compounds) obtained according to the above method with an oxidizing agent, corresponding epoxy group-containing polycyclic compounds represented by the formula (19) can be obtained.

As such oxidizing agents, there may be mentioned known or conventional oxidizing agents used in epoxidation of a nonaromatic ethylenic double bond, including peracetic acid, perbenzoic acid, m-chloroperbenzoic acid, monoperoxyphthalic acid, trifluoroperacetic acid, and other peracids; dioxyrane and other peroxides; hydroperoxides and hydrogen peroxides in the presence of a metal catalyst. The amount of the oxidizing agent is, for example, from about 1 to about 1.6 equivalents to the nonaromatic ethylenic double bond to be oxidized.

The reaction is usually performed in an organic solvent. As the organic solvent, any solvents inert to oxidation can be employed, including, for instance, the solvents described in the acylation reaction. The reaction may also be conducted in the presence of a basic substance such as sodium carbonate, sodium hydrogencarbonate, or sodium dihydrogenphosphate in a reaction system. The reaction temperature is, for instance, from about −10° C. to about 100° C.

After the completion of the reaction, the reaction product can be isolated and purified with facility, by a conventional isolation means such as filtration, concentration, distillation, extraction, crystallization, recrystallization or column chromatography, or any combination of these isolation means.

According to the aforementioned method, the adamantane derivatives represented by the formula (20), for example, can be produced. As the halogen atoms, alkyl groups, protective groups for hydroxyl group or the like, acyl groups, hydroxylmethyl groups which may have a substituent, and vinyl groups which may have a substituent in the $R^{c6}$, $R^{d6}$, and $R^{e6}$ in the formula (20) include similar groups to the halogen atoms, alkyl groups, and the like in the $R^{c4}$, $R^{d4}$, and $R^{e4}$. The "epoxy group which may have a substituent" in $R^{c6}$, $R^{d6}$, and $R^{e6}$ means an epoxy group formed by oxidation of the "vinyl group which may have a substituent" with the oxidizing agent; and $R^f$ and $R^g$ have the same meanings as defined above.

Of the adamantane derivatives represented by the formula (20), preferred adamantane derivatives include compounds in which at least one of $R^{c6}$, $R^{d6}$, and $R^{e6}$ is a hydroxyl group which may be protected by a protective group, a carboxyl group which may be protected by a protective group, an acyl group, a vinyl group which may have a substituent, or an epoxy group which may have a substituent. These compounds can enhance or impart a variety of functions, since they each have a reactive functional group in the adamantane ring.

Typical examples of the adamantane derivatives represented by the formula (20) include 3-(1,2-epoxyethyl)-1-adamantanol and its derivatives whose hydroxyl group is protected, 1-(1,2-epoxyethyl)-3-carboxyadamantane and its derivatives whose carboxyl group is protected, 1-acetyl-3-(1,2-epoxyethyl)adamantane, 1-(1,2-epoxyethyl)-3-vinyladamantane, and 1,3-bis(1,2-epoxyethyl)adamantane.

The epoxy group-containing polycyclic compounds obtained by the above method are useful as monomeric components of functional polymers (e.g., polyethers).

According to the acylating agent, the acylation method, and the method for the production of acyl group-containing compounds of the invention, an acyl group can directly be introduced with facility even to a carbon atom not activated (e.g., a methine carbon atom).

The method of the invention can provide acyl group-containing compounds, such as acyl group-containing adamantane derivatives, acyl group-containing tricyclo [5.2.1.0$^{2,6}$] decane derivatives and acyl group-containing decalin derivatives industrially with efficiency.

In addition, polycyclic compounds each having a vinyl group or epoxy group such as adamantane derivatives, tricyclo [5.2.1.0$^{2,6}$] decane derivatives and decalin derivatives each containing a vinyl group or epoxy group can be produced with efficiency.

According to the invention, novel adamantane derivatives, tricyclo [5.2.1.0$^{2,6}$] decane derivatives and decalin derivatives can be provided.

The present invention will now be described in more detail with reference to several examples below which are not directed to limiting the scope of the invention.

EXAMPLE 1

A mixture of 3 mmol of adamantane, 18 mmol of biacetyl, 0.015 mmol of cobalt(II) acetate, and 3 ml of acetic acid was stirred at 60° C. under an oxygen atmosphere (1 atm) for 4 hours. Gas chromatographic analysis of products in the reaction mixture revealed that adamantane was converted into, at a rate of 86%, 1-acetyladamantane (yield 50%), 1,3-diacetyladamantane (yield 23%), 1-acetyl-3-adamantanol (yield 4%), 1-adamantanol (yield 3%), and 2-adamantanone (yield 3%).

Spectrum Data of 1,3-diacetyladamantane

White solid substance

IR (cm$^{-1}$): 2932, 1706, 1453, 1344, 1253, 1192, 598
$^3$C-NMR (CDCl$_3$) δ: 24.4, 27.8, 35.5, 37.4, 38.5, 46.6, 212.9.

EXAMPLE 2

The procedure of Example 1 was repeated, except that the amount of cobalt (II) acetate was changed to 0.0015 mmol, to give 1-acetyladamantane (yield 29%), 1,3-diacetyladamantane (yield 35%), 1-acetyl-3-adamantanol (yield 10%), 1-adamantanol (yield 2%), and 2-adamantanone (yield 4%), at a conversion rate from adamantane of 97%.

EXAMPLE 3

By using 0.015 mmol of acetylacetonatocobalt (III) instead of cobalt (II) acetate, the procedure of Example 1 was repeated to give 1-acetyladamantane (yield 51%), 1,3-diacetyladamantane (yield 21%), 1-acetyl-3-adamantanol (yield 2%), 1-adamantanol (yield 2%), and 2-adamantanone (yield 3%), at a conversion rate from adamantane of 82%.

EXAMPLE 4

The procedure of Example 1 was repeated, except that 0.015 mmol of acetylacetonatovanadyl (II) was used instead of cobalt (II) acetate to give 1-acetyladamantane (yield 24%), 1,3-diacetyladamantane (yield 31%), 1-acetyl-3-adamantanol (yield 12%), 1-adamantanol (yield 3%), and 2-adamantanone (yield 3%), at a conversion rate from adamantane of 97%.

EXAMPLE 5

A mixture of 3 mmol of 1,3-dimethyladamantane, 18 mmol of biacetyl, 0.015 mmol of cobalt (II) acetate, and 3 ml of acetic acid was stirred at 60° C. under an oxygen atmosphere (1 atm) for 4 hours. Gas chromatographic analysis of products in the reaction mixture revealed that 1,3-dimethyladamantane was converted, at a rate of 93%, to 1-acetyl-3,5-dimethyladamantane (yield 40%), 1,3-diacetyl-5,7-dimethyladamantane (yield 15%), 1-acetyl-3,5-dmethyl-7-adamantanol (yield 5%), 1,3-dimethyl-5-adamantanol (yield 6%), and 1,3-dimethyl-4-adamantanone (yield 4%).

Spectrum Data of 1,3-diacetyl-5,7-dimethyladamantane

IR (cm$^{-1}$): 2923, 2847, 1696, 1454, 1359, 1191, 1155
$^{13}$C-NMR (CDCl$_3$) δ: 24.9, 30.4, 31.8, 37.8, 44.0, 49.0, 50.1, 212.9

Spectrum Data of 1-acetyl-3,5-dimethyl-7-adamantanol

IR (cm$^{-1}$): 3422, 2924, 1699, 1455, 1166, 1052, 600
$^{13}$C-NMR (CDCl$_3$) δ: 25.1, 29.8, 34.2, 43.8, 44.8, 49.8, 50.8, 51.4, 70.4, 212.6.

EXAMPLE 6

By using 0.03 mmol of cobalt (II) chloride instead of cobalt (II) acetate, the procedure of Example 5 was repeated to give 1-acetyl-3,5-dimethyladamantane (yield 34%), 1,3-diacetyl-5,7-dimethyladamantane (yield 13%), 1-acetyl-3,5-dimethyl-7-adamantanol (yield 5%), 1,3-dimethyl-5-adamantanol (yield 6%), and 1,3-dimethyl-4-adamantanone (yield 6%), at a conversion rate from 1,3-diacetyladamantane of 94%.

Comparative Example 1

The procedure of Example 5 was performed, except that a reaction was conducted under a nitrogen atmosphere instead of under an oxygen atmosphere. As a result, the reaction did not proceed.

EXAMPLE 7

A mixture of 3 mmol of 1,3-dimethyladamantane, 9 mmol of biacetyl, 0.0006 mmol of cobalt (II) acetate, and 3 ml of acetic acid was starred at 60° C. under an oxygen atmosphere(1 atm) for 4 hours. Gas chromatographic analysis of products in the reaction mixture demonstrated that 1,3-dimethyladamantane was converted, at a rate of 40%, to 1-acetyl-3,5 -dimethyladamantane (yield 8%, selectivity 20%), 1-acetyl-3,5-dimethyl-7-adamantanol (trace), 1,3-dimethyl-5-adamantanol (yield 17%, selectivity 43%), and 1,3-dimethyl-4-adamantanone (yield 5%, selectivity 13%).

EXAMPLE 8

The procedure of Example 7 was repeated, except that a mixture further comprising 0.3 mmol of N-hydroxyphthalimide in addition to the 1,3-dimethyladamantane, biacetyl, cobalt(II) acetate, and acetic acid was subjected to the reaction. As a result, 1-acetyl-3,5-dimethyladamantane (yield 19%, selectivity 53%), 1,3-diacetyl-5,7-dimethyladamantane (trace), 1-acetyl-3,5-dimethyl-7-adamantanol (trace), 1,3-dimethyl-5-adamantanol (yield 7%, selectivity 19%), and 1,3-dimethyl-4-adamantanone (yield 3%, selectivity 8%) were formed, at a conversion rate from 1,3-dimethyladamantane of 36%.

EXAMPLE 9

Except that the amount of biacetyl was changed to 18 mmol, the procedure of Example 8 was repeated to give 1-acetyl-3,5-dimethyladamantane (yield 18%, selectivity 29%), 1,3-diacetyl-5,7-dimethyladamantane (trace), 1-acetyl-3,5-dimethyl-7-adamantanol (yield 2%, selectivity 3%), 1,3-dimethyl-5-adamantanol (yield 24%, selectivity 38%), and 1,3-dimethyl-4-adamantanone (yield 5%, selectivity 38%), at a conversion rate from 1,3-dimethyladamantane of 63%.

EXAMPLE 10

Except that the amount of N-hydroxyphthalimide was changed to 0.6 mmol, the procedure of Example 9 was repeated to give 1-acetyl-3,5-dimethyladamantane (yield 32%, selectivity 54%), 1,3-diacetyl-5,7-dimethyladamantane (yield 2%, selectivity 3%), 1-acetyl-3,5-dimethyl-7-adamantanol (yield %, selectivity 2%), 1,3-dimethyl-5-adamantanol (yield 7%, selectivity 12%), and 1,3-dimethyl-4-adamantanone (yield 5%, selectivity 8%), at a conversion rate from 1,3-dimethyladamantane of 59%.

EXAMPLE 11

A mixture of 3 mmol of 1-adamantanol, 18 mmol of biacetyl, 0.015 mmol of cobalt (II) acetate, and 3 ml of acetic acid was stirred at 60° C. under an oxygen atmosphere (1 atm) for 4 hours. Products in the reaction mixture were found, by gas chromatographic analysis, to be 1-acetyl-3-adamantanol (yield 20%), 1,3-diacetyl-5-adamantanol (yield 5%), 1-acetyl-4-oxo-3-adamantanol and 1-acetyl-2-oxo-5-adamantanol (total yield 2%), 1,3-adamantanediol (yield 6%), and 4-oxo-1-adamantanol (yield 1%), at a conversion rate from 1-adamantanol of 82%.

Spectrum data of l-acetyl-3-adamantanol

IR (cm$^{-1}$) δ: 3401, 2897, 2854, 1683, 1430, 1019, 605
$^{13}$C-NMR (CDCl$_3$) δ: 24.3, 29.9, 34.8, 36.8, 43.9, 45.4, 49.6, 67.9, 212.4

Spectrum Data of 1,3-diacetyl-5-adamantanol

IR (cm$^{-1}$) δ: 3357, 2944, 1693, 1187, 1109
$^{13}$C-NMR (CDCl$_3$) δ: 25.0, 30.3, 36.6, 38.0, 43.5, 45.1, 50.0, 68.9, 212.0

Spectrum Data of 1-acetyl-4-oxo-3-adamantanol

MS m/e: 208 ([M$^+$]), 190, 175, 147, 119

Spectrum Data of 1-acetyl-2-oxo-5-adamantanol

MS m/e: 208 ([M$^+$]), 190, 175, 148, 119.

EXAMPLE 12

To 154 g of 1-acetyl adamantane obtained in a similar manner as in Example 1, were added 22 g of lithium aluminium hydride, and diethyl ether, and the resultant mixture was stirred at a temperature of from 0° C. to room temperature under a nitrogen atmosphere for 6 hours. To the reaction mixture was added 400 ml of water, and the resultant mixture was filtrated through Celite, and was concentrated to gave 87 g of 1-(1-hydroxyethyl)adamantane. To the obtained compound were added 400 ml of cyclohexane, 12 g of 97% sulfuric acid, and a small portion of hydroquinone, and the resultant mixture was stirred at 70° C. for 4 hours. The reaction mixture was distilled to give 27.9 g of 1-vinyladamantane (64° C./4 mmHg)

$^1$H-NMR (CDCl$_3$) δ: 1.4–1.9 (12H, m), 1.9–2.1 (3H, m), 4.8–4.95 (2H, m), 5.65–5.8 (1H, m) $^{13}$C-NMR (CDCl$_3$) δ: 28.5, 35.5, 37.0, 41.9, 108.8, 149.7.

Reference Example 1

A mixture of 110 g of 1-acetyladamantane obtained in the same manner as in Example 1, 900 ml of thionyl chloride, and 206 ml of pyridine was refluxed for 1 hour. After distilling off thionyl chloride and pyridine therefrom, the reaction mixture was extracted with hexane, and the extract was distilled to give 49 g of 1-(1-chloroethenyl)adamantane (123° C./11 mmHg)

IR (cm$^{-1}$): 876 (=CH$_2$), 733 (CCl), 665 $^{13}$C-NMR (CDCl$_3$) δ: 28.5, 36.7, 39.2, 40.7, 108.8, 153.3.

Reference Example 2

A mixture of 17.1 g of 1-acetyladamantane obtained in the same manner as in Example 1, 0.5 g of zinc iodide, 11.8 g of trimethylsilyl cyanide, and methylene chloride was stirred at 40° C. for 4 hours. The reaction mixture was concentrated, and was cooled to crystallize, and thereby to give 28.7 g of 1-(1-cyano-1-trimethylsilyloxyethyl)adamantane (white crystal).

The obtained 1-(1-cyano-1-trimethylsilyloxyethyl) adamantane was added to 45 ml of tetrahydrofuran and 17 ml of 2N-hydrochloric acid, and the resultant mixture was refluxed with stirring for 3 hours. After cooling the reaction mixture and adding an aqueous solution (water: 170 ml) of potassium hydrogencarbonate (11 g) thereto, the resultant mixture was extracted with ether, and the obtained organic layer was concentrated to give 24.1 g of 1-(1-cyano-1-hydroxyethyl)adamantane (white solid substance).

To the obtained 1-(1-cyano-1-hydroxyethyl) adamantane were added phosphorus oxychloride three times as much as the moles of the adamantane derivative, and170 ml of dried pyridine, and the resultant mixture was refluxed for 2 hours. Ether was added to the reaction mixture to a volume of 600 ml, and to this solution was added cooled 4N-hydrochloric acid (600 g) with stirring. The obtained organic layer was concentrated to give 17.4 g of 1-(1-cyanoethenyl) adamantane.

EXAMPLE 13

A mixture of 3 mmol of adamantane, 18 mmol of biacetyl, 0.3 mmol of N-hydroxyphthalimide, 0.015 mmol of cobalt (II) acetate, and 3 ml of acetic acid was stirred at 75° C. under an oxygen atmosphere (1 atm) for 10 hours. Gas chromatographic analysis of products in the reaction mixture revealed that adamantane was converted, at a rate of 100%, to 1-acetyladamantane (yield 52%), and 1-acetyl-3-adamantanol (yield 27%).

EXAMPLE 14

The procedure of Example 13 was repeated, except that the reaction temperature and reaction time were respectively changed to 85° C. and 6 hours, to give 1-acetyladamantane (yield 36%), 1-acetyl-3-adamantanol (yield 37%), and 1-acetyl-4-adamantanone and 1-acetyl-2-adamantanone (total yield 6%), at a conversion rate from adamantane of 100%.

Spectrum Data of 1-acetyl-4-adamantanone MS m/e: 192 ( [M$^+$]), 177, 149, 120

Spectrum Data of 1-acetyl-2-adamantanone MS m/e: 192 ([M$^+$]), 177, 148, 120.

EXAMPLE 15

The procedure of Example 13 was repeated, except that the reaction temperature and reaction time were respectively changed to 85° C. and 10 hours, to give 1-acetyladamantane (yield 25%), 1-acetyl-3-adamantanol (yield 32%), 1-acetyl-4-adamantanone (yield 4%), 1-acetyl-3,5-adamantanediol (yield 14%), 1-acetyl-4-oxo-3-adamantanol and 1-acetyl-2-oxo-5-adamantanol (total yield 8%) at a conversion rate from adamantane of 100%.

Spectrum Data of 1-acetyl-3,5-adamantanediol

IR (cm$^{-1}$) δ: 1050, 1204, 1347, 1456, 1695, 2932, 3317
$^{13}$C-NMR (CD$_3$OD) δ: 25.0, 32.1, 37.3, 43.8, 45.6, 52.2, 70.9, 214.

EXAMPLE 16

The procedure of Example 13 was repeated, except that the reaction temperature, reaction time and the amount of N-hydroxyphthalimide were changed to 85° C., 6 hours, and 0.6 mmol, respectively to give 1-acetyladamantane (yield 30%), 1-acetyl-3-adamantanol (yield 22%), 1,3-diacetyladamantane (yield 14%), and 1,3-diacetyl-5-adamantanol (yield 12%), at a conversion rate from adamantane of 100%.

EXAMPLE 17

A mixture of 3 mmol of 1-carboxyadamantane, 18 mmol of biacetyl, 0.3 mmol of N-hydroxyphthalimide, 0.015 mmol of cobalt (II) acetate, and 3 ml of acetic acid was stirred at 75° C. under an oxygen atmosphere (1 atm) for 6 hours. Gas chromatographic analysis of products in the reaction mixture demonstrated that 1-carboxyadamantane was converted, at a rate of 92%, to 1-acetyl-3-carboxyadamantane (yield 46%), and 1-acetyl-3-carboxy-5-adamantanol (yield 24%).

EXAMPLE 18

A mixture of 3 mmol of 1,3-dimethyladamantane, 18 mmol of biacetyl, 0.3 mmol of N-hydroxyphthalimide, 0.015 mmol of cobalt (II) acetate, and 3 ml of acetic acid was stirred at 75° C. under an oxygen atmosphere (1 atm) for 8 hours. Products in the reaction mixture were found, by gas chromatographic analysis, to be 1-acetyl-3,5-dimethyladamantane (yield 58%), and 1-acetyl-3,5-dimethyl-7-adamantanol (yield 22%) at a conversion rate of 1,3-dimethyladamantane of 94%.

EXAMPLE 19

The procedure of Example 18 was repeated, except that the reaction temperature and amount of N-hydroxyphthalimide were changed to 85° C. and 0.6 mmol, respectively, to give 1-acetyl-3,5-dimethyladamantane (yield 41%), 1-acetyl-3,5-dimethyl-7-adamantanol (yield 11%), and 1,3-d-acetyl-5,7-dimethyladamantane (yield 27%), at a conversion rate of 1,3-dimethyladamantane of 100%.

EXAMPLE 20

A mixture of 3 mmol of endotricyclo [5.2.1.0$^{2,6}$] decane, 18 mmol of biacetyl, 0.3 mmol of N-hydroxyphthalimide, 0.015 mmol of cobalt (II) acetate, and 3 ml of acetic acid was stirred at 75° C. under an oxygen atmosphere (1 atm) for 6 hours. Gas chromatographic analysis of products in the reaction mixture revealed that endotricyclo [5.2.1.0$^{2,6}$] decane was converted, at a rate of 75%, to 2-acetylendotricyclo [5.2.1.0$^{2,6}$] decane (yield 27%), 2-hydroxyendotricyclo [5.2.1.0$^{2,6}$] decane (yield 11%), 2,6-dihydroxyendotricyclo [5.2.1.0$^{2,6}$] decane (yield 16%), and dicyclo [5.2.1] decane-2,6-dione (yield 12%).

Spectrum Data of 2-acetyl endotricyclo [5.2.1.0$^{2,6}$] decane

MS m/e: 178 ( [M$^+$]), 163, 135.

EXAMPLE 21

A mixture of 3 mmol of cis-decalin, 18 mmol of biacetyl, 0.3 mmol of N-hydroxyphthalimide, 0.015 mmol of cobalt (II) acetate, and 3 ml of acetic acid was stirred at 75° C. under an oxygen atmosphere (1 atm) for 8 hours. Products in the reaction mixture were found, by gas chromatographic analysis, to be 4a-acetyl-cis-decalin (yield 24%), 4a-hydroxy-cis-decalin (yield 4%), 4a,8a-dihydroxy-is-decalin (yield 22%), and 1,6-cyclodecanedione (yield 10%), at a conversion rate from cis-decalin of 67%.

Spectrum Data of 4a-acetyl-cis-decalin

MS m/e: 180 ([M$^+$]), 165, 137

EXAMPLE 22

A mixture of 3 mmol of 1-acetyladamantane, 18 mmol of biacetyl, 0.015 mmol of cobalt(II) acetate, and 3 ml of acetic acid was stirred at 60° C. under an oxygen atmosphere (1 atm) for 4 hours. Products in the reaction mixture were found, by gas chromatographic analysis, to be 1,3-diacetyladamantane (yield 34%), 1-acetyl-3-adamantanol (yield 29%), and 1,3-diacetyl-5-adamantanol (yield 2%), 1-acetyl-4-adamantanone (yield 5%), at a conversion rate from 1-acetyladamantane of 80%.

EXAMPLE 23

Powdery sodium borohydride (4.8 g) was added slowly over 30 minutes to a mixture of 45.0 g of 1-acetyladamantane, 100 ml of methanol, and 20 ml of 0.1 N sodium hydroxide on a water bath. The resultant mixture was further stirred for 30 minutes, was neutralized with a 1 N hydrochloric acid aqueous solution, and 200 ml of water was added to the mixture. The obtained crystals were filtrated, was washed with water and was dried in vacuo to give 45.0 g of 1-(1-hydroxyethyl)adamantane. To this were added 400 ml of toluene, 4.9 g of 98% sulfuric acid, and 0.1 g of hydroquinone, and the resultant mixture was stirred for 3 hours with azeotropic distillation and dehydration. The reaction mixture was cooled, washed with saturated aqueous sodium bicarbonate and saturated sodium chloride aqueous solution, and was concentrated. The obtained concentrate was distilled to give 29.0 g (yield 72.5%) of 1-vinyladamantane (65° C./4 mm Hg).

Spectrum Data of 1-acetyladamantane $^1$H-NMR (CDCl$_3$) δ: 1.65–1.85 (m, 12H), 2.00–2.10 (m, 3H), 2.10 (s, 3H)

Spectrum Data of 1-(1-hydroxyethyl)adamantane $^1$H-NMR (CDCl$_3$) δ: 1.10 (d, 3H), 1.30–1.40 (br, 1H), 1.42–1.80 (m, 12H), 1.90–2.10 (m, 3), 3.29 (q, 1H)

Spectrum Data of 1-vinyladamantane $^1$H-NMR (CDCl$_3$) δ: 1.50–1.80 (m, 12H), 1.90–2.05 (m, 3H), 4.80–4.90 (m, 2H), 5.71 (dd, 1H)

To a mixture of 16.2 g of 1-vinyladamantane, 120 ml of dichloromethane, and 5.3 g of sodium carbonate, 36.9 g of 70-m-chloroperbenzoic acid was added over 30 minutes on a water bath. The resultant mixture was stirred at room temperature for further 2 hours, was washed with a 5% sodium sulfite aqueous solution and saturated aqueous sodium bicarbonate, and the obtained organic layer was then concentrated. The residue was purified by column chromatography on a silica gel (SiO$_2$400 g, developing solution: hexane/ethyl acetate=15/1) to give 11.0 g of 1-(1,2-epoxyethyl)adamantane.

Spectrum Data of 1-(1,2-epoxyethyl)adamantane $^1$H-NMR (CDCl$_3$) δ: 1.45–1.80 (m, 12H), 1.90–2.05 (m, 3H), 2.55–2.64 (m, 2H), 2.65–2.70 (m, 1H).

EXAMPLE 24

A total of 1 g of sodium borohydride was slowly added to a mixture of 5.6 g of 1,3-diacetyladamantane, 20 ml of methanol, and 3 ml of 0.1 N sodium hydroxide aqueous solution on a water bath. After stirring for 30 minutes at room temperature, the resultant mixture was neutralized with a 1 N hydrochloric ac4d aqueous solution. To the neutralized mixture was added 50 ml of water, and the resultant mixture was extracted with three portions of 100 ml of ethyl acetate. The obtained organic layer was concentrated to give 5.5 g of 1,3-bis(1-hydroxyethyl)adamantane.

Toluene (100 ml), 98% sulfuric acid (0.5 g), hydroquinone (0.02 g) were added to this product, and the resultant mixture was stirred for 5 hours with azeotropic distillation and dehydration. The reaction mixture was cooled, was washed with a saturated aqueous sodium bicarbonate and saturated sodium chloride aqueous solution, and was then concentrated. The residue was purified by column chromatography on a silica gel ($SiO_2$ 100 g, developing solution: hexane) to give 3.0 g of 1,3-divinyladamantane.

Spectrum Data of 1,3-divinyladamantane $^1$H-NMR ($CDCl_3$) δ: 1.30–1.80 (m, 12H), 1.90–2.10 (m, 3H), 4.70–5.05 (m, 2H), 5.73 (dd, 1H) A total of 12.6 g of powdery 70%-m-chloroperbenzoic acid was added, slowly over 30 minutes, to a mixture of 3.6 g of 1,3-divinyladamantane, 50 ml of dichloromethane, and 1.8 g of sodium carbonate on a water bath. The resultant mixture was further stirred at room temperature for 2 hours, was washed with a 5% sodium sulfite aqueous solution and a saturated aqueous sodium bicarbonate, and the organic layer thus obtained was concentrated. The residue was purified by column chromatography on a silica gel ($SiO_2$ 80 g, developing solution: hexane/ethyl acetate=15/1) to give 2.6 g of 1,3-bis(1,2 -epoxyethyl)adamantane.

Spectrum Data of 1,3-bis(1,2-epoxyethyl) adamantane $^1$H-NMR ($CDCl_3$) δ: 1.30–1.80 (m, 12H), 1.90–2.10 (m, 3H), 2.55–2.65 (m, 4H), 2.65–2.75 (m, 2H)

EXAMPLE 25

A total of 0.6 g of sodium borohydride was slowly added to a mixture of 4.0 g of 2-acetyl-1-adamantanol, 20 ml of methanol, and 2 ml of a 0.1 N sodium hydroxide aqueous solution on a water bath. After stirring at room temperature for 30 minutes, the resultant mixture was neutralized with a 1 N hydrochloric acid aqueous solution. To the neutralized mixture was added 50 ml of water, and the resultant mixture was extracted with three portions of 100 ml of ethyl acetate. The organic layer thus obtained was concentrated to give 3.6 g of 3-(1-hydroxyethyl)-1-adamantanol.

To 3 g of 3-(1-hydroxyethyl)-1-adamantanol were added 60 ml of toluene, 0.4 g of 98% sulfuric acid, and 0.01 g of hydroquinone, and the resultant mixture was stirred for 5 hours with azeotropic distillation and dehydration. The reaction mixture was cooled, was washed with a saturated aqueous sodium bicarbonate and saturated sodium chloride aqueous solution, and was then concentrated. The residue was purified by column chromatography on a silica gel ($SiO_2$ 80 g, developing solution: hexane/ethyl acetate=10/1) to give 1.5 g of 3-vinyl-1-adamantanol.

A total of 3.2 g of powdery 70%-m-chloroperbenzoic acid was slowly added over 30 minutes to a mixture of 1.5 g of 3-vinyl-1-adamantanol, 25 ml of dichloromethane, and 2.3 g of sodium carbonate on a water bath. The resultant mixture was further stirred at room temperature for 2 hours, was washed with a 5% sodium sulfite aqueous solution and a saturated aqueous sodium bicarbonate, and the organic layer thus obtained was concentrated. The residue was purified by column chromatography on a silica gel ($SiO_2$ 40 g, developing solution: hexane/ethyl acetate=5/1) to give 0.45 g of 3-(1,2-epoxyethyl)-1-adamantanol.

Spectrum data of 3-(1,2-epoxyethyl)-1-adamantanol
$^1$H-NMR ($CDCl_3$) δ: 1.40–1.80 (m, 13H), 2.20–2.30 (m, 2H), 2.55–2.65 (m, 2H), 2.65–2.75 (m, 1H).

What is claimed is:

1. An acylating agent being composed of
(A) a compound represented by the following formula (2a):

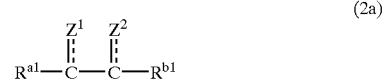

(2a)

wherein each of $R^{a1}$ and $R^{b1}$ is, identical to or different from each other, an alkyl group having 1 to 4 carbon atoms, a cycloalkyl group, or an aryl group, or $R^{a1}$ and $R^{b1}$ when taken together form a cyclopentyl or cyclohexyl ring with the adjacent two carbon atoms to which they are attached; and each of $Z^1$ and $Z^2$ is, identical to or different from each other, an oxygen atom or a hydroxyl group, (B) oxygen, and (C) at least one compound selected from (C1) a metallic compound selected from the group consisting of an elementary metal, a metallic hydroxide, a metallic oxide, a metallic halide, a metallic salt of an oxo acid, an oxo acid containing a metal, an isopolyacid containing a metal, a heteropolyacid containing a metal, a metallic salt of an organic acid, and a metallic complex and (C2) an imide compound represented by the following formula (1):

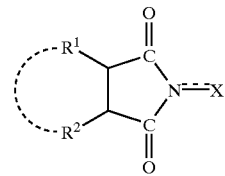

(1)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, and $R^1$ and $R^2$ when taken together form a double bond, or a 5- to 12-membered aromatic or nonaromatic ring; X is an oxygen atom or a hydroxyl group; and one or two N-substituted cyclic imido groups indicated in the formula (1) may be bonded to the aforementioned $R^1$, $R^2$, or to the double bond or aromatic or nonaromatic ring formed together by $R^1$ and $R^2$.

2. The acylating agent according to claim 1, wherein said 1,2-dicarbonyl compound or its hydroxy reductant (A) is biacetyl, acetoin, or 2,3-butanediol.

3. The acylating agent according to claim 1, wherein said metallic compound (C1) is a transition metal compound.

4. The acylating agent according to claim 3, wherein said transition metal compound is a cobalt compound or a vanadium compound.

5. An acylation method comprising the step of reacting a polycyclic organic compound having a methine carbon at a bridgehead position with the acylating agent of claim 1 to give a polycyclic organic compound containing an acyl group.

6. The acylation method according to claim 5, wherein said polycyclic compound has an adamantane ring, a tricyclo [5.2.1.0$^{2,6}$] decane ring, or a decalin ring.

7. A method for the production of an adamantane compound, said method comprising the step of reacting an adamantane compound represented by the following formula (3):

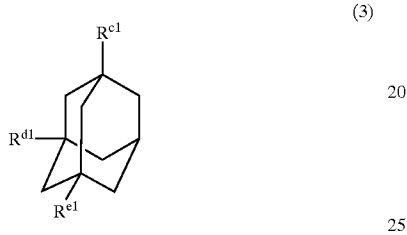

(3)

wherein each of $R^{c1}$, $R^{d1}$ and $R^{e1}$ is, identical to or different from one another, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group, a carboxyl group which is protected by a protective group, a nitro group, or an acyl group; and the adamantane carbon atoms other than those at the bridgehead position may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group with the acylating agent of claim 1, to give a compound represented by the following formula (4):

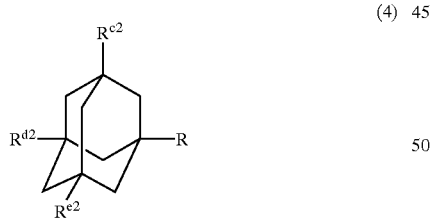

(4)

wherein R is an acyl group, and each of $R^{c2}$, $R^{d2}$, and $R^{e2}$ is, identical to or different from one another, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group, a carboxyl group which is protected by a protective group, a nitro group, or an acyl group; the adamantane carbon atoms other than those at the bridgehead position may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group.

8. An adamantane compound represented by the following formula (7):

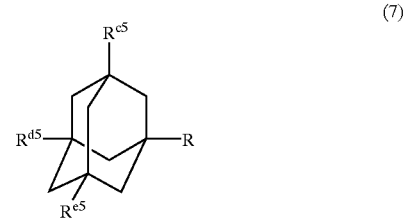

(7)

wherein R is an acyl group, $R^{c5}$ is a hydroxyl group, or an acyl group, and each of $R^{d5}$ and $R^{e5}$ is, identical to or different from each other, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group, a carboxyl group which is protected by a protective group, a nitro group, or an acyl group; and the adamantane carbon atoms other than those at the bridgehead position may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group; provided that when $R^{c5}$ is a hydroxyl group, at least one of $R^{d5}$ and $R^{e5}$ is other than a hydrogen atom, or provided that one or more of the carbon atoms constituting the adamantane structure, other than those at the bridgehead positions, bears an oxo group.

9. A method for the production of a tricyclodecane compound, said method comprising the step of reacting a tricyclodecane compound represented by the following formula (11):

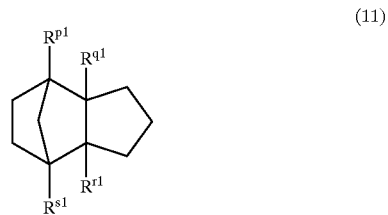

(11)

wherein each of $R^{p1}$, $R^{q1}$, $R^{r1}$ and $R^{s1}$ is, identical to or different from one another, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group, a carboxyl group which is protected by a protective group, a nitro group, or an acyl group, provided that at least one of $R^{p1}$, $R^{q1}$, $R^{r1}$ and $R^{s1}$ is a hydrogen atom; and the tricyclodecane carbon atoms other than those at the bridgehead positions may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group with the acylating agent of claim 1 to acylate a bridgehead position, and thereby to give a compound represented by the following formula (12):

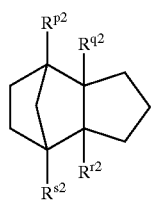

(12)

wherein each of $R^{p2}$, $R^{q2}$, $R^{r2}$ and $R^{s2}$ is, identical to or different from one another, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group, a carboxyl group which is protected by a protective group, a nitro group, or an acyl group, provided that at least one of $R^{p2}$, $R^{q2}$, $R^{r2}$ and $R^{s2}$ is an acyl group; and the tricyclodecane carbon atoms other than those at the bridgehead positions may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group.

10. A tricyclodecane compound represented by the following formula (12):

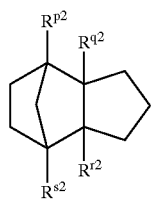

(12)

wherein each of $R^{p2}$, $R^{q2}$, $R^{r2}$ and $R^{s2}$ is, identical to or different from one another, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group, a carboxyl group which is protected by a protective group, a nitro group, or an acyl group, provided that at least one of $R^{q2}$ and $R^{r2}$ is an acyl group; and the tricyclodecane carbon atoms other than those at the bridgehead positions may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group.

11. A method for the production of a decalin compound, said method comprising the step of reacting a decalin compound represented by the following formula (13):

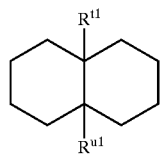

(13)

wherein each of $R^{r1}$ and $R^{u1}$ is, identical to or different from each other, a hydrogen atom, a halogen atom, an alkyl group, a hydroxyl group, a hydroxyl group which is protected by a protective group, a hydroxymethyl group, a hydroxylmethyl group which is protected by a protective group, an amino group, an amino group which is protected by a protective group, a carboxyl group, a carboxyl group which is protected by a protective group, a nitro group, or an acyl group, provided that at least one of $R^{r1}$ and $R^{u1}$ is a hydrogen atom; and the decalin carbon atoms than those at the bridgehead positions may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group with the acylating agent of claim 1, to acylate a bridgehead position, and thereby to give a compound represented by the following formula (14):

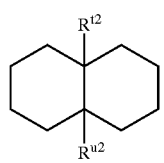

(14)

wherein each of $R^{r2}$ and $R^{u2}$ is, identical to or different from each other, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group, a carboxyl group which is protected by a protective group, a nitro group, or an acyl group, provided that at least one of $R^{r2}$ and $R^{u2}$ is an acyl group; and the decalin carbon atoms other than those at the bridgehead positions may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group.

12. A decalin compound represented by the following formula (14):

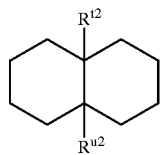

(14)

wherein each of $R^{r2}$ and $R^{u2}$ is, identical to or different from each other, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group, a carboxyl group which is protected by a protective group, a nitro group, or an acyl group, provided that at least one of $R'^2$ and $R''^2$ is an acyl group; and the decalin carbon atoms other than those at the bridgehead positions are unsubstituted.

13. A method for the production of a vinyl-substituted polycyclic compound, said method comprising the steps of: reacting a polycyclic compound represented by the following formula (15):

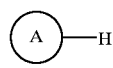
(15)

wherein the ring A is a polycyclic group having a methine carbon atom at the bridgehead position, and the single bond indicated in the formula is bonded to said bridgehead position with an acylating agent being composed of (A1) a compound represented by the following formula (2b)

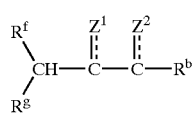
(2b)

wherein each of $R^f$, $R^g$ and $R^b$ is, identical to or different from one another, a hydrogen atom, a hydrocarbon group or a heterocyclic group; and each of $Z^1$ and $Z^2$ is, identical to or different from each other, an oxygen atom or a hydroxyl group, (B) oxygen, and (C) at least one compound selected from (C1) a metallic compound and (C2) an imide compound represented by the following formula (1):

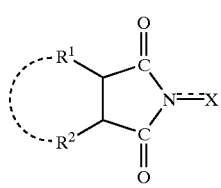
(1)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ when taken together form a double bond, or a 5- to 12-membered aromatic or nonaromatic ring; X is an oxygen atom or a hydroxyl group; and to the aforementioned $R^1$, $R^2$, or to the double bond or aromatic or nonaromatic ring formed together by $R^1$ and $R^2$, one or two N-substituted cyclic imido groups indicated in the formula (1) may be bonded to give a compound represented by the following formula (16):

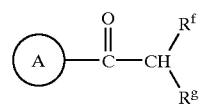
(16)

wherein the ring A, $R^f$ and $R^g$ have the same meanings as defined above, reducing the obtained compound represented by the formula (16) by reduction with a metal hydride complex compound, reduction using borane, or catalytic reduction to give a compound represented by the following formula (17):

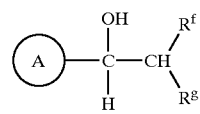
(17)

wherein the ring A, $R^f$ and $R^g$ have the same meanings as defined above, and subjecting the compound represented by the formula (17) to dehydration reaction at a temperature of from about 0° C. to about 150° C. to give a compound represented by the following formula (18):

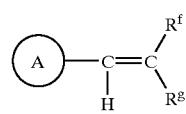
(18)

wherein the ring A, $R^f$ and $R^g$ have the same meanings as defined above.

14. The method for the production of a vinyl-substituted polycyclic compound according to claim 13; wherein said polycyclic compound represented by the formula (15) is an adamantane compound represented by the following formula (3):

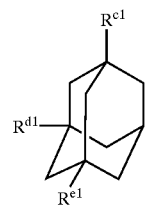
(3)

wherein each of $R^{c1}$, $R^{d1}$ and $R^{e1}$ is, identical to or different from one another, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group, a carboxyl group which is protected by a protective group, a nitro group, or an acyl group; and the adamantane carbon atoms other than those at the bridgehead positions may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group, a tricyclo decane compound represented by the following formula (11):

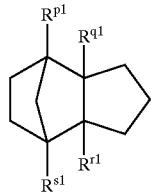

(11)

wherein each of $R^{p1}$, $R^{q1}$, $R^{r1}$ and $R^{s1}$ is, identical to or different from one another, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group, a carboxyl group which is protected by a protective group, a nitro group, or an acyl group, provided that at least one of $RP^1$, $R^{q1}$, $R^{r1}$ and $R^{s1}$ is a hydrogen atom; and of carbon atoms the tricyclodecane carbon atoms other than those at the bridgehead positions may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group, or a decalin compound represented by the following formula (13):

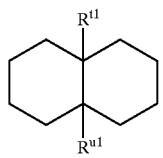

(13)

wherein each of $R^{t1}$ and $R^{u1}$ is, identical to or different from each other, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group, a carboxyl group which is protected by a protective group, a nitro group, or an acyl group, provided that at least one of $R^{t1}$ and $R^{u1}$ is a hydrogen atom; and the decalin carbon atoms other than those at the bridgehead positions may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group.

15. A method for the production of a polycyclic compound containing an epoxy moiety, said method comprising the step of reacting a vinyl-substituted polycyclic compound obtained by the method of claim 13 or claim 14 and represented by the following formula (18):

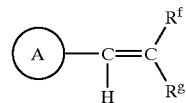

(18)

wherein the ring A is a polycyclic ring having a methine carbon atom at the bridgehead position, and the single bond indicated in the formula is bonded to said bridgehead position; and each of $R^f$ and $R^g$ is, identical to or different from each other, a hydrogen atom, a hydrocarbon group or a heterocyclic group with an oxidizing agent to give a compound represented by the following formula (19):

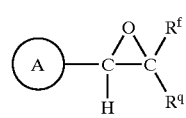

(19)

wherein the ring A, $R^f$, and $R^g$ have the same meanings as defined above.

16. An adamantane compound represented by the following formula (20):

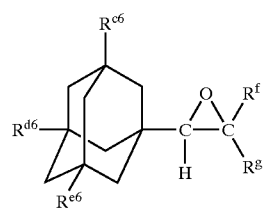

(20)

wherein each of $R^{c6}$, $R^{d6}$, and $R^{e1}$ is, identical to or different from one another, a hydrogen atom, a halogen atom, an alkyl group, a hydroxyl group, a hydroxyl group which is protected by a protective group, a hydroxymethyl group, a hydroxymethyl group which is protected by a protective group, an amino group, an amino group which is protected by a protective group, a carboxyl group a carboxyl group which is protected by a protective group, a nitro group, an group, a hydroxymethyl group which may have a substituent that is a functional group formed by reducing an acyl group, a vinyl group which may have a substituent that is a functional group formed by dehydrating the hydroxymethyl group which may have a substituent, or an epoxy group which may have a substituent that is formed by oxidation of the vinyl group which may have a substituent, provided that $R^{c6}$, $R^{d6}$, and $R^{e6}$ are not concurrently hydrogen atoms; each of $R^f$ and $R^g$ is, identical to or different from each other, a hydrogen atom, a hydrocarbon group or a heterocyclic group; and the adamantane carbon atoms other than those at the bridgehead positions may each have a substituent selected from the group consisting of an oxo group, an alkyl group, an acyl group, a hydroxyl group, an alkoxy group, an acyloxy group, a carboxyl group, an alkoxycarbonyl group, a halogen atom, and a cyano group.

17. The acylating agent according to claim 4, wherein said metallic compound is a cobalt compound selected from the group consisting of cobalt hydroxide, cobalt oxide, cobalt chloride, cobalt bromide, cobalt nitrate, cobalt sulfate, cobalt phosphate, a cobalt salt of an organic acid, and a cobalt complex.

18. The acylating agent according to claim 4, wherein said metallic compound is a vanadium compound selected from the group consisting of vanadium hydroxide, vanadium oxide, vanadium chloride, vanadyl chloride, vanadium sulfate, vanadyl sulfate, sodium vanadate, and a vanadium complex.

19. The acylating agent according to claim 1, wherein said hydroxy reductant is selected from the group consisting of an alpha-keto-alcohol and a vicinal diol.

20. The acylating agent according to claim 1, wherein said hydroxy reductant is an alpha-keto alcohol selected from the group consisting of acetoin and benzoin.

21. The acylating agent according to claim 1, wherein said hydroxy reductant is a vicinal diol selected from the group consisting of 2,3-butanediol and 2,3-pentanediol.

22. The acylating agent according to claim 4, wherein said metallic compound comprises a cobalt compound selected from the group consisting of cobalt hydroxide, cobalt oxide, cobalt chloride, cobalt bromide, cobalt nitrate, cobalt sulfate, cobalt phosphate, cobalt salts of organic acids, and cobalt complexes.

23. The acylating agent according to claim 4, wherein said metallic compound comprises a vanadium compound selected from the group consisting of vanadium hydroxide, vanadium oxide, vanadium chloride, vanadyl chloride, vanadium sulfate, vanadyl sulfate, sodium vanadate, and vanadium complexes.

24. The acylating agent according to claim 1, wherein the imide compound (C2) is selected from the group consisting of N-hydroxysuccinimide, N-hydroxymaleimide, N-hydroxyhexahydrophthalimide, N,N'-dihydroxycyclohexanetetracarboximide, N-hydroxyphthalimide, N-hydroxy-tetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

* * * * *